(12) United States Patent
Stein et al.

(10) Patent No.: US 8,469,950 B2
(45) Date of Patent: Jun. 25, 2013

(54) INTRA-ATRIAL APPARATUS AND METHOD OF USE THEREOF

(75) Inventors: Uri Stein, Rishon LeZion (IL); Nathan Sela, Modiln (IL)

(73) Assignee: Cardionova Ltd., Ariel (IL)

( * ) Notice: Subject to any disclaimer, the term of this patent is extended or adjusted under 35 U.S.C. 154(b) by 754 days.

(21) Appl. No.: 12/526,796

(22) PCT Filed: Feb. 3, 2008

(86) PCT No.: PCT/IL2008/000147
§ 371 (c)(1),
(2), (4) Date: Aug. 12, 2009

(87) PCT Pub. No.: WO2008/099380
PCT Pub. Date: Aug. 21, 2008

(65) Prior Publication Data
US 2010/0030204 A1   Feb. 4, 2010

Related U.S. Application Data

(60) Provisional application No. 60/901,315, filed on Feb. 15, 2007.

(51) Int. Cl.
*A61B 18/04* (2006.01)
*A61B 18/02* (2006.01)

(52) U.S. Cl.
USPC .............................................. 606/27; 606/20

(58) Field of Classification Search
USPC ................................. 606/20, 27, 41
See application file for complete search history.

(56) References Cited

U.S. PATENT DOCUMENTS

| 5,575,810 A | 11/1996 | Swanson |
| 5,766,151 A | 6/1998 | Valley |
| 5,769,846 A | 6/1998 | Edwards |
| 6,237,605 B1 | 5/2001 | Vaska |
| 6,645,199 B1 * | 11/2003 | Jenkins et al. ............. 606/41 |
| 6,997,925 B2 | 2/2006 | Maguire |
| 2003/0187428 A1 * | 10/2003 | Lane et al. ............. 606/21 |
| 2004/0034347 A1 * | 2/2004 | Hall et al. ............. 606/41 |

(Continued)

FOREIGN PATENT DOCUMENTS

| EP | 1698296 A | 9/2006 |
| WO | 9501751 | 1/1995 |
| WO | 9600041 | 1/1996 |
| WO | 0067656 | 11/2000 |
| WO | 2004105807 | 12/2004 |
| WO | 2007001981 | 1/2007 |

OTHER PUBLICATIONS

International search report for corresponding PCT/IL2008/000147 dated Feb. 3, 2008.

(Continued)

*Primary Examiner* — Michael Peffley
*Assistant Examiner* — Samantha Good
(74) *Attorney, Agent, or Firm* — Graeser Associates International Inc; D'vorah Graeser

(57) ABSTRACT

An intra-atrial ablation therapy apparatus is disclosed. The apparatus comprises a balloon adapted for intra-atrial inflation to fill at least part of the atrium, the balloon being adapted to permit a flow of blood from a pulmonary vein to a mitral valve when inflated in the atrium. The apparatus further comprises an inflation lumen being in fluid communication with the balloon and adapted for conducting an inflation fluid to the balloon. The apparatus also comprises an ablation tool connected to the catheter.

3 Claims, 22 Drawing Sheets

U.S. PATENT DOCUMENTS

| | | | |
|---|---|---|---|
| 2004/0106920 A1* | 6/2004 | Jenkins et al. | 606/49 |
| 2004/0153060 A1* | 8/2004 | Lindenbaum et al. | 606/49 |
| 2004/0260277 A1 | 12/2004 | Maguire | |
| 2005/0070887 A1 | 3/2005 | Taimisto | |
| 2005/0070888 A1 | 3/2005 | Dimatteo | |
| 2005/0251125 A1* | 11/2005 | Pless et al. | 606/27 |
| 2007/0219546 A1 | 9/2007 | Mody | |

OTHER PUBLICATIONS

Office action for EP087101153.1 dated Mar. 16, 2010.
Office action for IL200394 dated May 7, 2012.

* cited by examiner

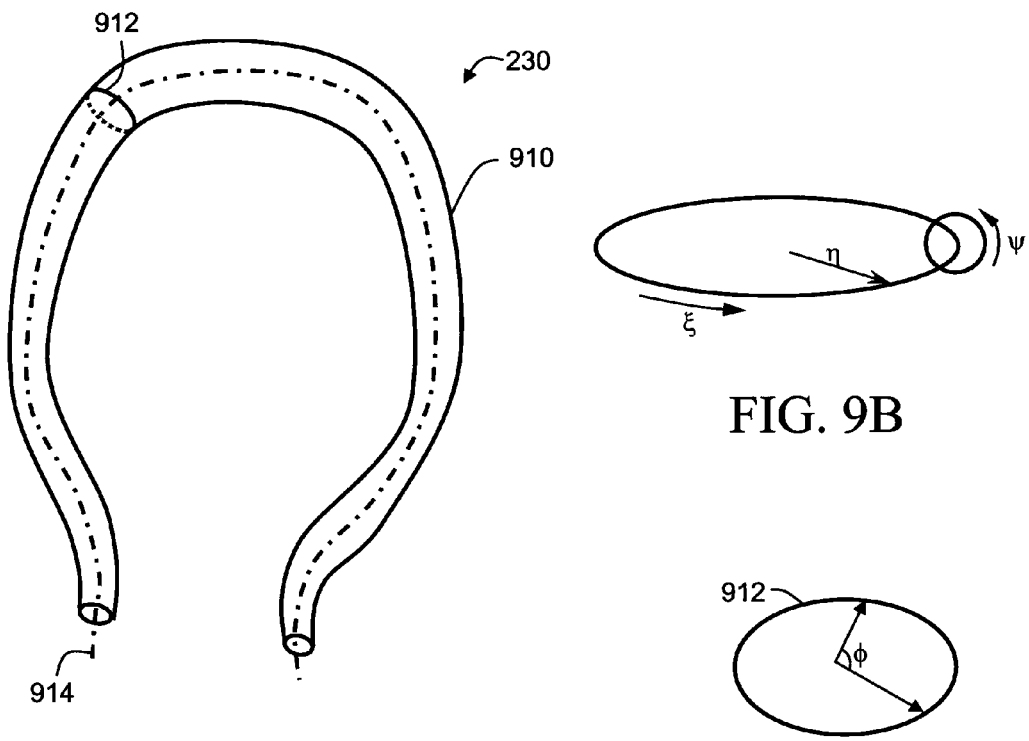
FIG. 9A
FIG. 9B
FIG. 9C
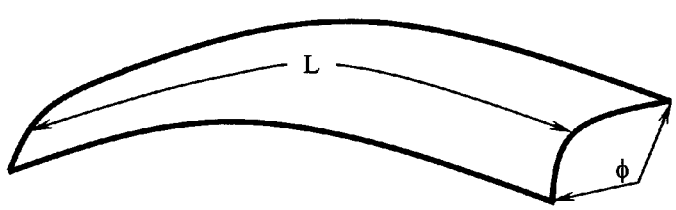
FIG. 9D
FIG. 9E

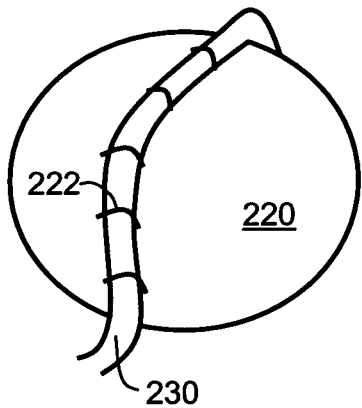
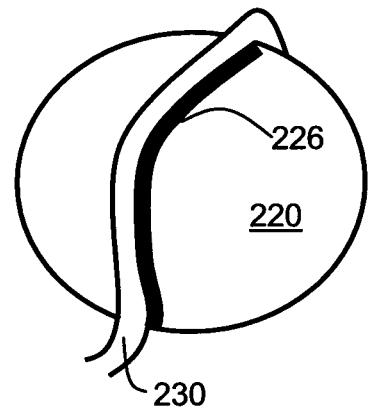
FIG. 13A          FIG. 13B
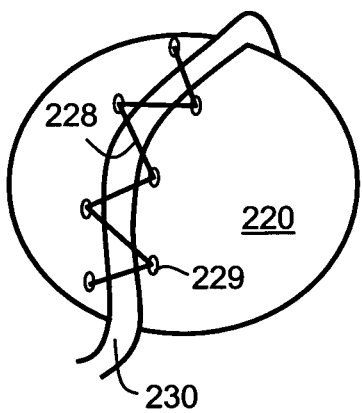
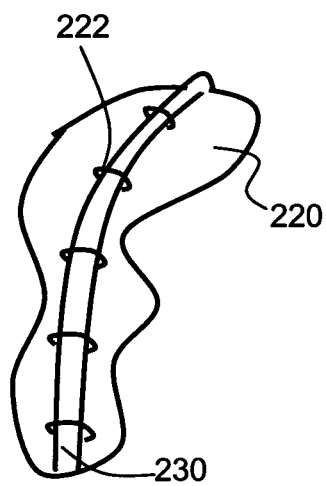
FIG. 13C          FIG. 13D
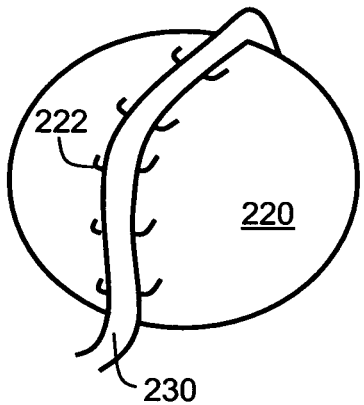
FIG. 13E

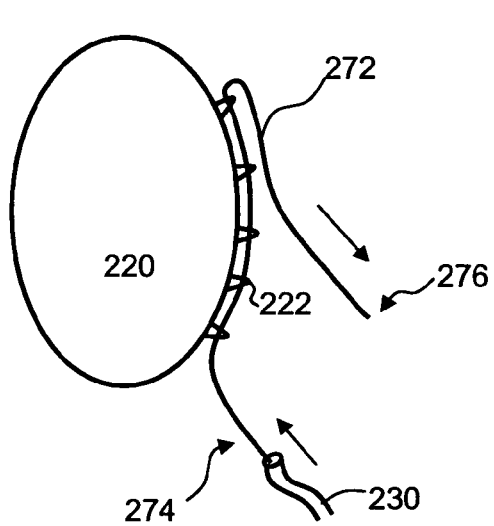
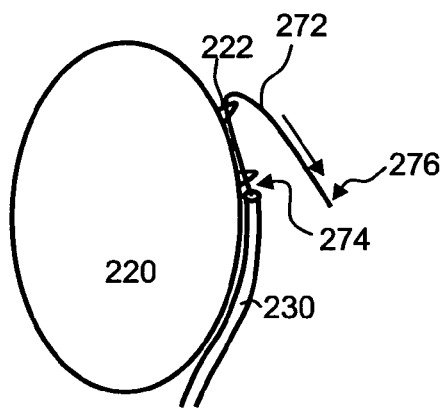
FIG. 14A  FIG. 14B
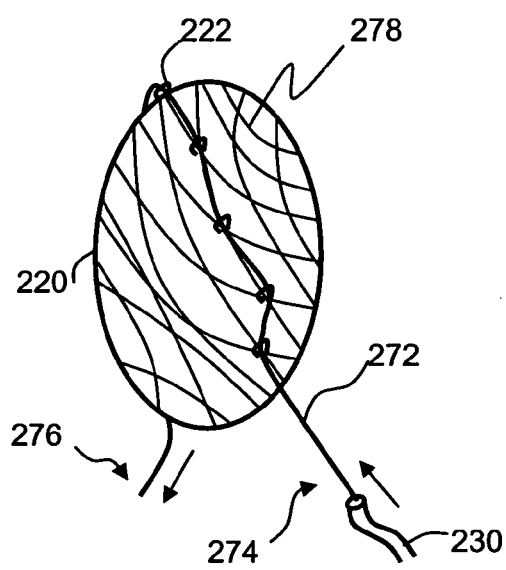
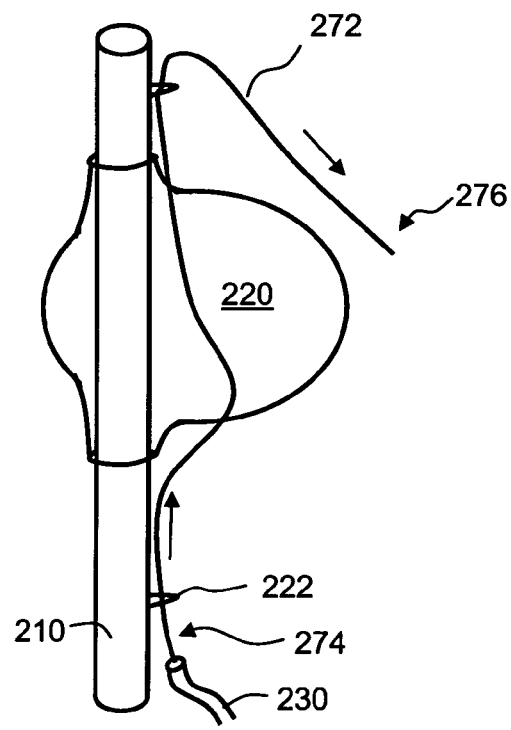
FIG. 14C  FIG. 14D

INTRA-ATRIAL APPARATUS AND METHOD OF USE THEREOF

This Application is a national phase of, and claims priority from, PCT Application No. PCT/IL2008/000147 having International Filing date of Feb. 3, 2008, which claims priority from U.S. Provisional Application No. 60/901,315, filed on Feb. 15, 2007, all of which are hereby incorporated by reference as if fully set forth herein.

FIELD AND BACKGROUND OF THE INVENTION

The present invention, in some embodiments thereof, relates to intra-atrial therapy and, more particularly, but not exclusively, to a medical apparatus and a method for performing intra-atrial ablation therapy.

An objective of intra-atrial ablation therapy is to isolate a defined portion of an atrium from an electrical signal. During pursuit of this objective, disruption of blood flow in a heart chamber can be a problem.

U.S. Pat. No. 5,575,810 discloses an inelastic balloon with an attached inelastic ablation element for use in a heart chamber. The described balloon provides an inner flow channel for blood. The disclosure of this patent is fully incorporated herein by reference.

WO 04/105807 describes an expanding "clover" shaped balloon to bring a circular ablation element into contact with an inner surface of a pulmonary vein. The described clover configuration leaves channels for blood flow between the balloon and an inner surface of the pulmonary vein so that flowing blood can contact the inner surface of the pulmonary vein. The disclosure of this application is fully incorporated herein by reference.

U.S. Pat. No. 6,237,605 and U.S. Pat. No. 6,997,925 each describe a continuous electrically insulated boundary encircling the pulmonary veins as a means to electrically isolate the pulmonary veins from the myocardium. Both of these patents describe epicardial ablation procedures. The disclosures of each of these patents are fully incorporated herein by reference.

U.S. Pat. No. 5,769,846 describes a balloon that fills an atrium of a heart. The disclosure of this patent is fully incorporated herein by reference.

SUMMARY OF THE INVENTION

An aspect of some embodiments of the invention relates to a balloon configuration which leaves an open path from one or more pulmonary blood vessels to the mitral valve when the balloon is inflated in a heart chamber. Optionally, the balloon is asymmetric. In an exemplary embodiment of the invention, the balloon fills at least 20% of an atrial volume. In various exemplary embodiments of the invention the balloon fills 70, 80, 90% or more of the atrial volume.

An aspect of some embodiments of the invention relates to formation of a continuous ablation line surrounding four pulmonary veins in the atria with a single application of an ablation tool. Optionally, the ablation tool is a cryo-ablation tool. In an exemplary embodiment of the invention, 50, 60, 70, or 80% or intermediate or greater percentages of atrial tissue remains in electrical contact with signals emanating from a sino-atrial (SA) node after formation of the ablation line, i.e., the signals reach the tissue.

An aspect of some embodiments of the invention relates to a balloon comprising at least two independently inflatable chambers so that an ablation tool associated with the balloon can be steered to a desired target by inflating the chambers to different degrees. Optionally, three or four or more independently inflatable chambers are provided.

An aspect of some embodiments of the invention relates to an elastic balloon adapted for atrial insertion with at least one slideably attached element connected to the balloon by a series of rings so that a distance between adjacent rings increases as the balloon is inflated. The rings can also be connected to a net of strings stretched over the balloon. In an exemplary embodiment of the invention, the slideable element is flexible. In exemplary embodiments of the invention the slideable element can be elastic or inelastic. In an exemplary embodiment of the invention, the balloon fills 70, 80, or 90% or more of an atrial volume.

An aspect of some embodiments of the invention relates to inflating a balloon within an atrium to direct an ablation tool towards a target and initiating an ablation process which causes the ablation tool to remain in contact with or adhere to the target. In an exemplary embodiment of the invention, the balloon at least partially deflated and the ablation tool continues to remain in contact with or adhere to the target. For example, upon deflation of the balloon (e.g., towards the catheter body) the ablation tool can be disconnected from the balloon. Optionally, the ablation tool is a cryo-ablation tool.

In an exemplary embodiment of the invention, deflation causes the balloon to collapse towards the ablation tool. Optionally, collapse towards the ablation tool permits blood to flow between the balloon and an atrial wall.

In an exemplary embodiment of the invention, deflation causes the balloon to collapse towards the ablation tool. Optionally, collapse towards the ablation tool permits blood to flow between the balloon and an atrial wall.

In an exemplary embodiment of the invention, the ablation tool is provided on a secondary balloon mounted on a main balloon. Optionally, the ablation tool is slideably attached to the secondary balloon. In an exemplary embodiment of the invention, the secondary balloon, or a spacer, permits blood flow between the ablation tool and the main balloon in proximity to an ablation target during ablation. Optionally, the secondary balloon insulates a portion of the ablation tool and prevents unwanted changes in blood temperature. In an exemplary embodiment of the invention, the ablation tool is a cryo-ablation tool and insulation prevents unwanted cooling, or freezing, of blood.

An aspect of some embodiments of the invention relates to ejection of contrast solution or dye, such as a radio-opaque contrast material, from ports provided on an elastic balloon to determine an orientation of an ablation tool associated with a balloon in a heart chamber. In an exemplary embodiment of the invention, contrast solution is ejected from one or more holes in a channel in or on the balloon. After ejection, the dye is observed via medical imaging (e.g. fluoroscopy). In an exemplary embodiment of the invention, if dye is observed in one or more pulmonary veins, positioning is presumed to be correct.

According to an aspect of some embodiments of the present invention there is provided an intra-atrial ablation therapy apparatus. The apparatus comprises a balloon adapted for intra-atrial inflation to fill at least part of the atrium, and an inflation lumen in fluid communication with the balloon and being adapted for conducting an inflation fluid thereto. In various exemplary embodiments of the invention the balloon is adapted to permit a flow of blood from a pulmonary vein to a mitral valve when inflated in the atrium.

According to some embodiments of the invention the balloon is asymmetric.

According to some embodiments of the invention the balloon is adapted to occupy at least 70% of an atrial volume when inflated in the atria.

According to some embodiments of the invention an outer surface the balloon comprises at least one structural element constructed so as to allow blood flow between the outer surface and an inner wall of the atrium.

According to some embodiments of the invention the structural element is selected from the group consisting of protrusions extending from the outer surface and slits formed in the outer surface.

According to some embodiments of the invention the apparatus comprises an expandable ablation tool configured as a loop, and a catheter adapted to deliver the ablation tool and the balloon to the atria.

According to an aspect of some embodiments of the present invention there is provided apparatus adapted for intra-atrial ablation therapy, the apparatus comprises: a balloon adapted for intra-atrial inflation, and an ablation tool passing through a plurality of rings attached to or integrally formed with a surface of the balloon. The ablation tool passes through the rings such that inflation of the balloon causes the ablation tool to expand.

According to some embodiments of the invention the apparatus comprises a spacer positioned between the ablation tool and the balloon, the spacer adapted to prevent contact between a portion of the balloon and an inner wall of the atrium.

According to some embodiments of the invention the spacer comprises an additional balloon.

According to some embodiments of the invention the ablation tool comprises a cryo-ablation element.

According to some embodiments of the invention a longitudinal section of the ablation tool is characterized in that a thermal conductivity of a first circumferential section of the longitudinal section is higher than the thermal conductivity of at least one second circumferential section of the longitudinal section, the at least one second circumferential section being complementary to the first circumferential section.

According to some embodiments of the invention the ablation tool comprises an ablation element which ablates by heating.

According to some embodiments of the invention the loop of the ablation tool is connected to additional tool material in the catheter.

According to some embodiments of the invention supply of additional tool material from the catheter causes expansion of the loop.

According to some embodiments of the invention expansion of the loop moves additional tool material from the catheter to the loop.

According to some embodiments of the invention inflation of the balloon causes the ablation tool to expand and move towards an ablation location.

According to some embodiments of the invention the apparatus comprises an arrangement of rings installed on a surface of the balloon, the ablation tool passing through the rings such that inflation of the balloon causes the ablation tool to expand.

According to some embodiments of the invention at least one of the balloon and the catheter comprises an arrangement of rings adapted for receiving a guidewire for guiding the ablation tool to an ablation location.

According to still further features in the described preferred embodiments the apparatus further comprises a net of strings stretched over at least part of a surface of the balloon, and an arrangement of rings connected to the net.

According to some embodiments of the invention the ablation tool is mounted on an outer surface of the balloon.

According to some embodiments of the invention the ablation tool is mounted by a connection mechanism selected such that when the balloon is inflated the ablation tool is detached from the outer surface of the balloon.

According to some embodiments of the invention the ablation tool is embedded in a wall of the balloon.

According to some embodiments of the invention the ablation tool is disposed within an inner cavity of the balloon.

According to some embodiments of the invention the balloon comprises at least two independently inflatable chambers.

According to still further features in the described preferred embodiments the apparatus further comprises an inflation controller adapted to independently inflate each of the chambers of the balloon, wherein a relative position of the ablation tool with respect to an ablation location is adjustable by regulating a degree of inflation of each of the chambers.

According to some embodiments of the invention the ablation tool is constructed primarily of a metal.

According to an aspect of some embodiments of the present invention there is provided a method of intra-atrial ablation, comprising inserting a balloon and an ablation tool into an atrium, inflating the balloon, and activating the ablation tool in an ablation location in a manner such that an ablation line is formed around the ablation location.

According to some embodiments of the invention the inflation of the balloon is performed while the ablation tool is mounted on the balloon.

According to some embodiments of the invention the inflation of the balloon is performed while the ablation tool is detached from the balloon and the ablation tool is delivered to the ablation location subsequently to the inflation.

According to an aspect of some embodiments of the present invention there is provided a method of insuring blood flow through an atrium having a plurality of pulmonary veins and a mitral valve, during an ablation procedure. The method comprises: (a) inflating a balloon within an atrium to direct an ablation tool towards a desired tissue; (b) activating the ablation tool so that the ablation tool contacts the desired tissue; (c) at least partially deflating the balloon to open a flow path from at least one pulmonary vein to the mitral valve, while leaving the tool in contact with the desired tissue.

According to some embodiments of the invention inserting is via a trans-septal route.

According to some embodiments of the invention the ablation location comprises all four pulmonary veins.

According to some embodiments of the invention the ablation line comprises a hemi-atrial ablation line.

According to some embodiments of the invention the ablation tool comprises an interior lumen and the activating comprises inducing a flow of fluid through the lumen.

According to some embodiments of the invention the ablation line leaves at least 50% of atrial tissue in electrical contact with a signal emanating from a sino-atrial node.

According to some embodiments of the invention the ablation tool is provided as a cryo-ablation tool and activating includes causing a cold fluid to flow through the ablation tool.

According to an aspect of some embodiments of the present invention there is provided apparatus for verifying a placement of an ablation tool, the apparatus comprising: a balloon adapted to inflate to fill at least 50% of an atrium; an ablation tool mounted on the balloon; and at least one contrast solution channel including at least one contrast injection port mounted on the balloon.

According to some embodiments of the invention the apparatus comprises a contrast injector adapted to inject contrast solution from the at least one contrast injection port.

According to some embodiments of the invention the apparatus comprises an imaging module adapted to image the contrast solution.

According to some embodiments of the invention the contrast injection port is surrounded by the loop of the ablation material.

According to some embodiments of the invention the imaging module comprises a fluoroscopy device.

According to some embodiments of the invention the imaging module is aimed to provide an image of pulmonary veins and presence of contrast solution in the pulmonary veins indicates a correct placement of the ablation tool.

According to an aspect of some embodiments of the present invention there is provided a controller for controlling an intra-atrial ablation apparatus, the controller comprising: (a) an ablation control component adapted to control an operational state of an ablation tool configured for intra-atrial ablation; and (b) a pump interface adapted for: (i) inflation of at least one balloon deployed in an atrium; and (ii) alteration of a shape of the ablation control component.

According to some embodiments of the invention the ablation control component comprises a pump interface.

According to some embodiments of the invention the ablation control component comprises a voltage controller.

According to some embodiments of the invention the controller comprises a contrast injector adapted to cause contrast solution to flow through at least one contrast injection port.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 9A-E and 10A-D are fragmentary schematic illustrations showing an ablation tool, according to various exemplary embodiments of the present invention;

FIGS. 13A-E are schematic illustrations of connection types between the ablation tool and the balloon, according to various exemplary embodiments of the present invention;

FIGS. 14A-D are schematic illustrations of embodiments in which the ablation tool and the balloon are initially disengaged, and the deployment of the ablation tool is executed subsequently to the inflation of the balloon in the atrium.

Figure 1A:
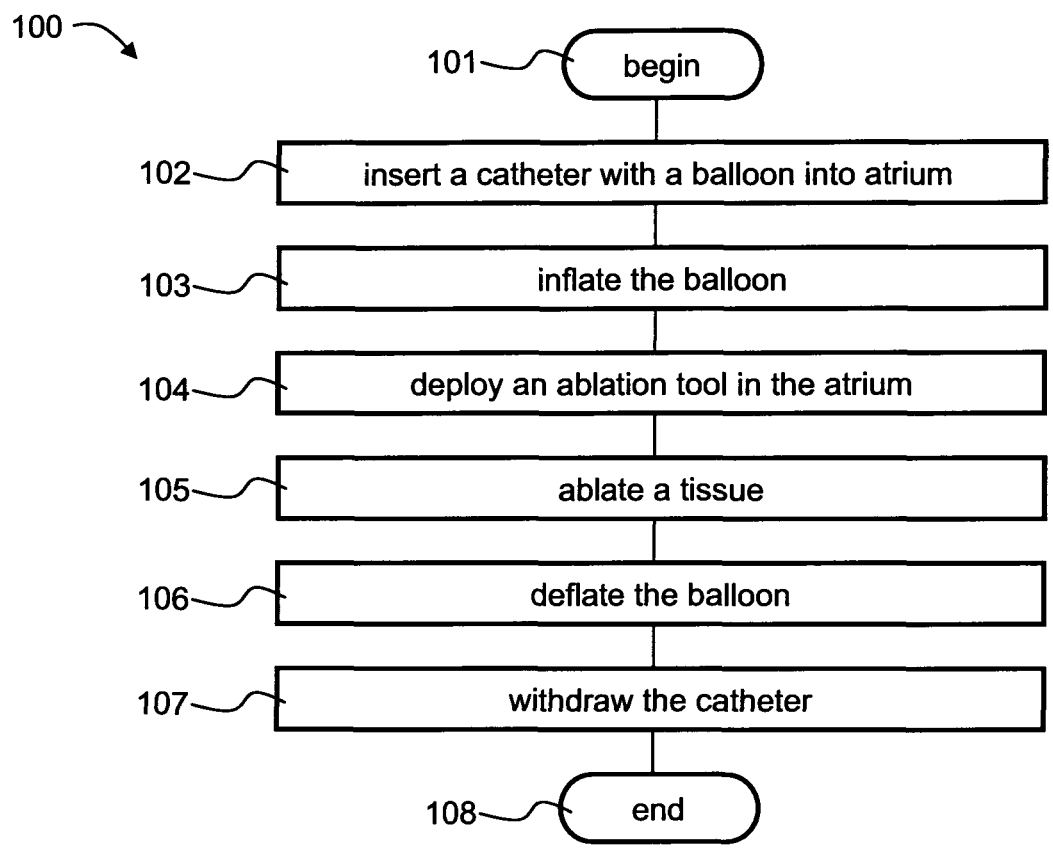
FIGS. 1A-B are simplified flowchart diagrams illustrating methods according to exemplary embodiments of the invention.

DESCRIPTION OF SPECIFIC EMBODIMENTS
OF THE INVENTION

The present invention, in some embodiments thereof, relates to intra-atrial therapy and, more particularly, but not exclusively, to a medical apparatus and a method for performing intra-atrial ablation therapy.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Overview

Figure 1B:
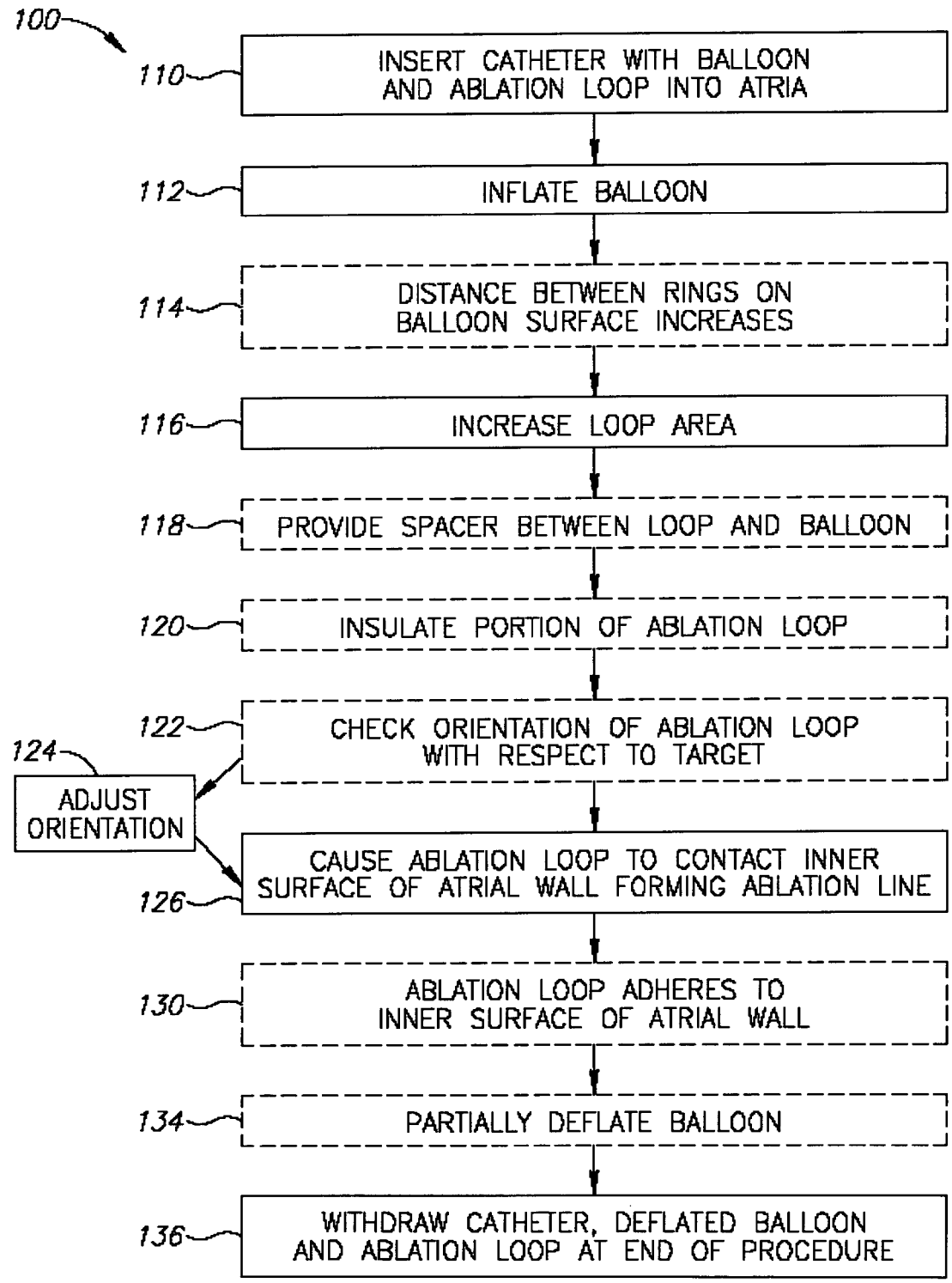
Figure 2A:
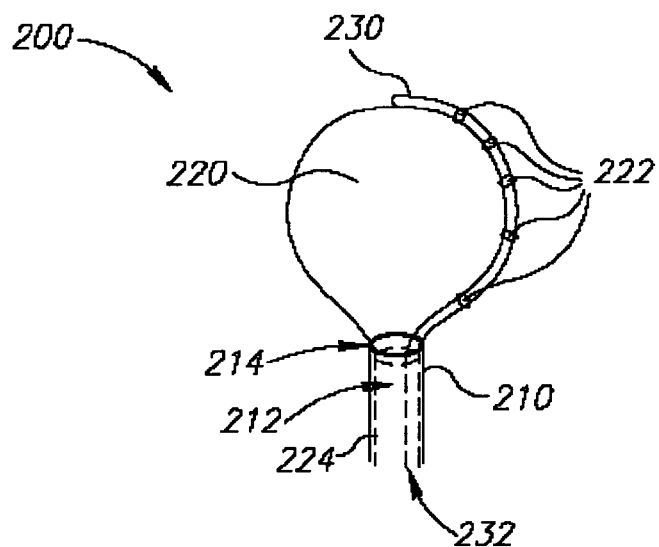
FIGS. 2A-B are side and front views respectively of an exemplary balloon and ablation catheter according to one exemplary embodiment of the invention.
Figure 2B:
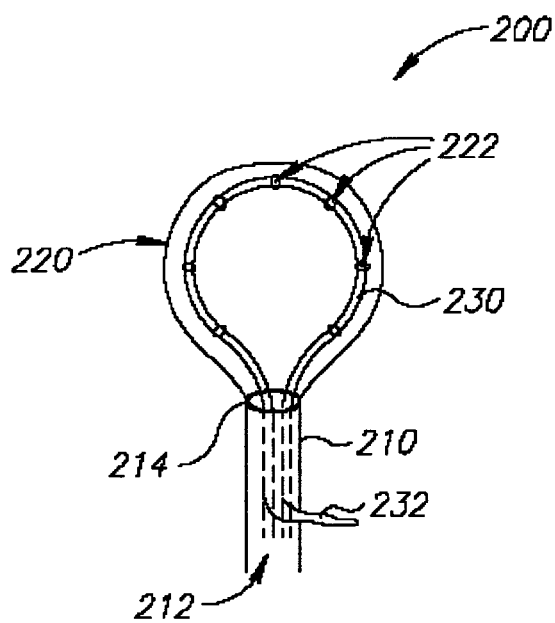

FIGS. 2A and 2B are side and front views respectively of an intra-atrial ablation apparatus 200 according to an exemplary embodiment of the invention. Apparatus 200 and additional exemplary embodiments of the invention are described in the context of a method 100 (FIGS. 1A-B) and other figures which depict additional features of exemplary embodiments of the invention. Various depicted exemplary embodiments of the invention have in common a balloon 220 and an ablation tool 230 deployable from a distal end 214 of a catheter 210. Other optional features are depicted in other figures and described below.

Exemplary Intra-Atrial Ablation Procedure

FIG. 1A is a simplified flowchart diagram illustrating an exemplary intra-atrial ablation procedure 100. Ablation procedure 100 employs balloons 220 and ablation tools 230 in various configurations as depicted in the other figures.

It is to be understood that, unless otherwise defined, method steps or stages described hereinbelow can be executed either contemporaneously or sequentially in many combinations or orders of execution. Specifically, the ordering of the flowchart diagrams is not to be considered as limiting. For example, two or more method steps or stages, appearing in the following description or in the flowchart diagrams in a particular order, can be executed in a different order (e.g., a reverse order) or substantially contemporaneously. Additionally, several method steps or stages described below are optional and may not be executed.

Ablation procedure 100 begins at 101.

At 102 a catheter 210 is inserted into the atrium 280 (see, for example, FIGS. 2A-C) of a subject (not shown). A balloon 220 is mounted on catheter 210 such that insertion of catheter 210 results in deployment of balloon 220 in atrium 280. Balloon 220 can be made stretchable (e.g., elastic) or non-stretchable with a certain degree of characteristic strain (e.g., about 300% or higher for stretchable balloon and 20% or lower for non-stretchable). In any event, balloon 220 is inflatable. The term "balloon" as used herein refers to a single balloon or an arrangement of balloons.

Optionally, an ablation tool 230 is also mounted on catheter 210 such that upon insertion of catheter 210, ablation tool 230 is delivered to the cavity of atrium 280 together with balloon 220. Ablation tool 230 can be, for example, a cryo-ablation or a heat ablation tool. Ablation tool 230 can be mounted on balloon 220 or catheter 210, as further detailed hereinunder.

At 103 balloon 220 is inflated within atrium 280. When ablation tool 230 is mounted on balloon 220, the inflation of the balloon results in deployment 104 of tool 230 to engage an ablation location 285 (see FIG. 2C) in atrium 280. When ablation tool 230 is not mounted on balloon 220, deployment 104 is optionally by delivering (e.g., by a string or guidewire already in place) ablation tool 230 to ablation location 285. At 104 ablation tool 230 is activated to ablate the tissue at ablation location 285. Activation of ablation tool 230 can be done either by generating a flow of cold fluid (e.g., a biocompatible cryogenic fluid such as, but not limited to, carbon dioxide, nitrous oxide, liquid nitrogen and fluorocarbon), or by electrical activation of ablation energy (e.g., resistive heat, ultrasound and radiofrequency).

Following the ablation procedure 100 optionally proceeds to 106 in which balloon 106 is deflated and 107 in which catheter 210 is withdrawn. Procedure 100 ends at 108.

Selected procedural phases are described in more details hereinbelow with reference to FIG. 1B which is a more detailed flowchart diagram of selected phases of procedure 100.

At 110 an ablation apparatus 200 comprising catheter 210 carrying balloon 220 and ablation tool 230 is inserted into an atrium 280. Optionally, insertion is via a trans-septal approach as illustrated in FIGS. 2C, 2D, 3C, 3D, 7A and 7B.

At 112, balloon 220 is inflated. In an exemplary embodiment of the invention, inflation of balloon 220 brings ablation tool 230 into proximity with a target on an inner wall 282 of atrium 280.

Figure 8A:
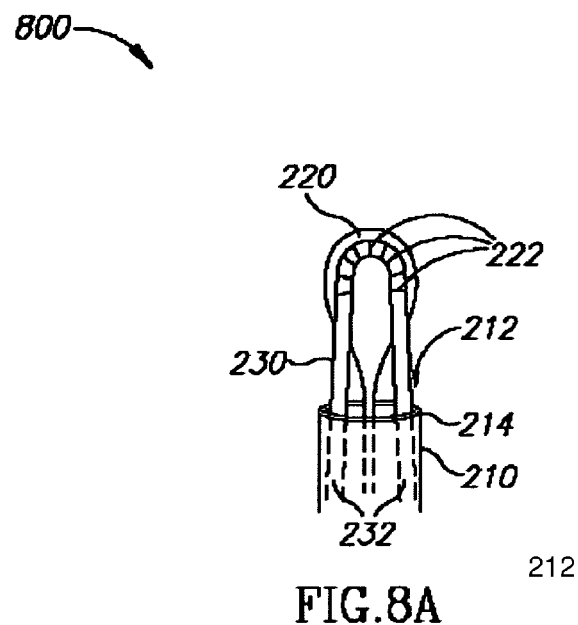
FIGS. 8A-B illustrate an exemplary slideable connection between an ablation tool and a balloon according to some embodiments of the invention.
Figure 8B:
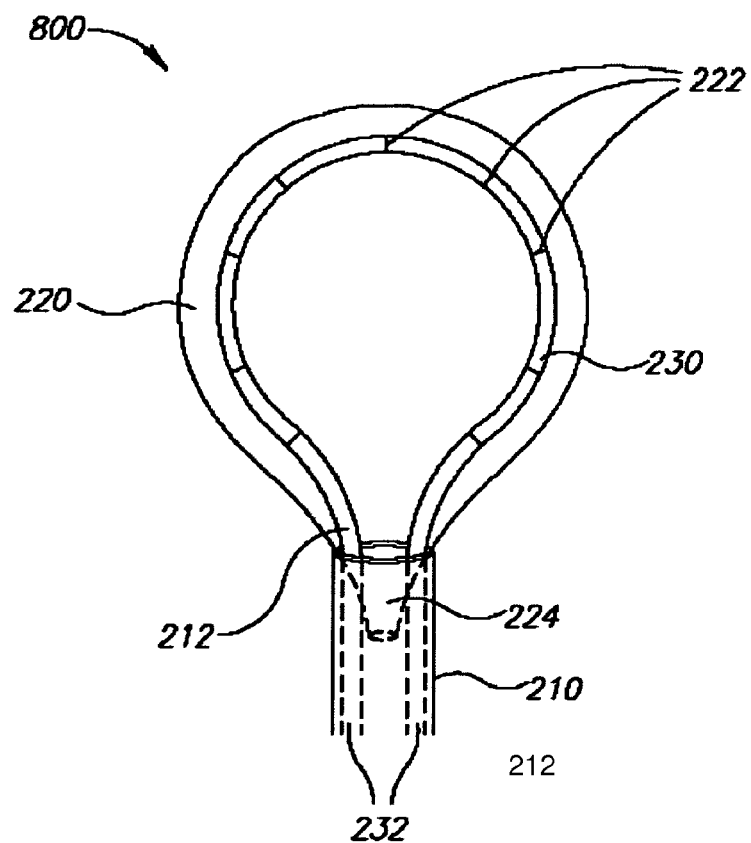

In an exemplary embodiment of the invention, inflation 112 causes an increase 114 in a distance between rings 222 on a surface of balloon 220 (best seen in FIGS. 8A and 8B). Rings 222 are typically, but not obligatorily, adapted to engage ablation tool 230 at an engagement point which is fixed with respect to balloon 220 and slideable with respect to ablation tool 230. Optionally, the increase in distance 114 causes an increase 116 in an area of ablation tool 230, for example by causing tool 230 to expand to form a loop.

In some exemplary embodiments of the invention, a spacer 340 is provided 118) between ablation tool 230 and balloon 220 (see FIGS. 3A, 3B, 3C and 3D). Rings 222 are not shown in FIGS. 3A, 3B, 3C and 3D for clarity although they are optionally present. In an exemplary embodiment of the invention, rings 222 on balloon 220 engage ablation tool 230 and spacer 340. Rings 222 can either be connected directly to the balloon or they can be connected to a net stretched over the balloon (see, e.g., FIG. 14C). In an exemplary embodiment of the invention, spacer 340 contributes to an increase in blood flow between inner wall 282 of atrium 280 and balloon 220. Optionally, spacer 340 insulates 120 at least a portion of ablation tool 230. In an exemplary embodiment of the invention, loop 230 is a cryo-ablation tool and insulation 120 contributes to a reduction in unwanted cooling of tissue (e.g. blood) outside the target. In an exemplary embodiment of the invention, loop 230 is a heat generating loop and insulation 120 contributes to a reduction in unwanted heating of tissue (e.g. blood) outside the target.

In an exemplary embodiment of the invention, an orientation of expanded ablation tool 230 with respect to the target is checked 122 after inflation 112. Optionally, orientation of a loop of ablation tool 230 with respect to the target is adjusted 124. In an exemplary embodiment of the invention, checking 122 is by means of contrast material injection as described in detail hereinbelow with regard to FIG. 5. Optionally, checking 122 is by means of a camera (not shown) mounted in balloon 220.

In an exemplary embodiment of the invention, the loop of tool 230 contacts 126 an inner wall 282 of atria 280 forming an ablation line. Optionally, the loop of tool 230 adheres, sticks or otherwise remains in contact 130 to inner wall 282 of atria 280 as a result of contact 126 during or before ablation.

Figure 3A:
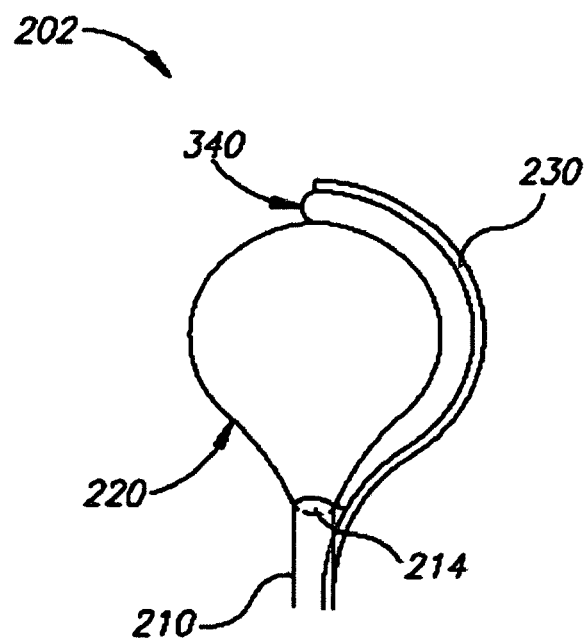
FIGS. 3A-B are side and front views respectively of an exemplary balloon and ablation catheter according to another exemplary embodiment of the invention.
Figure 3B:
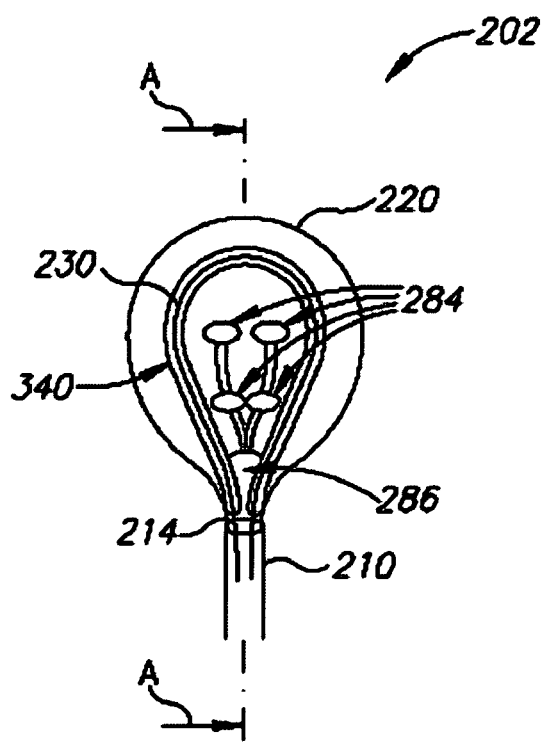
Figure 3C:
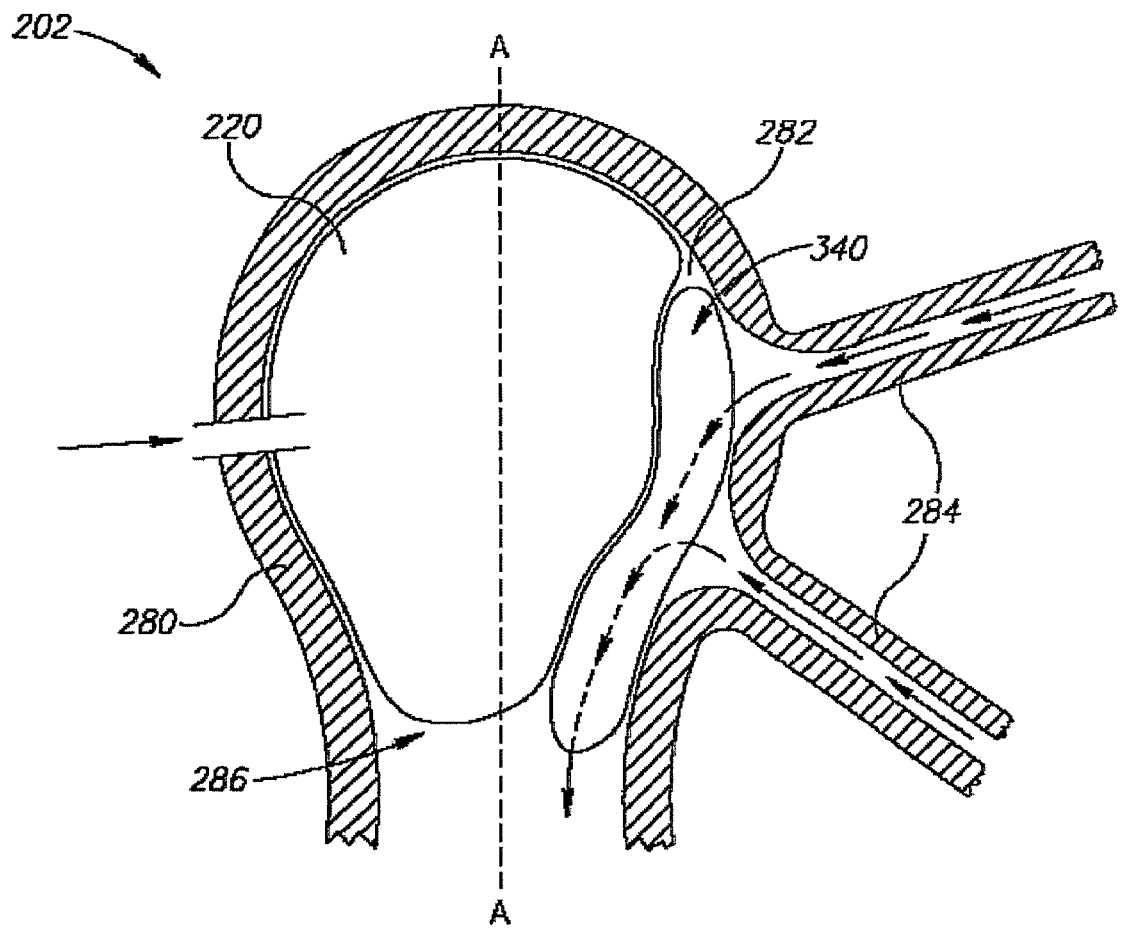
FIGS. 3C-D are cross sections of an atrium showing exemplary positioning of an ablation element by a balloon according to exemplary embodiments of the invention.
Figure 3D:
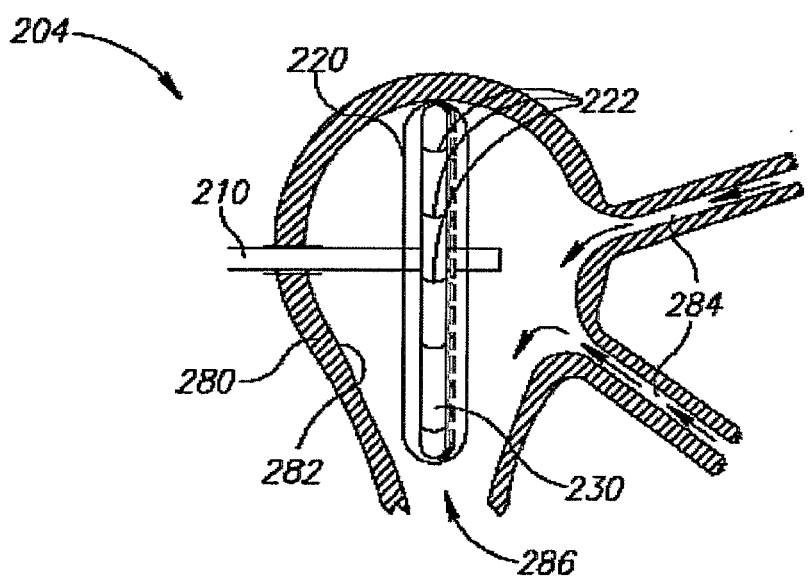
Figure 7A:
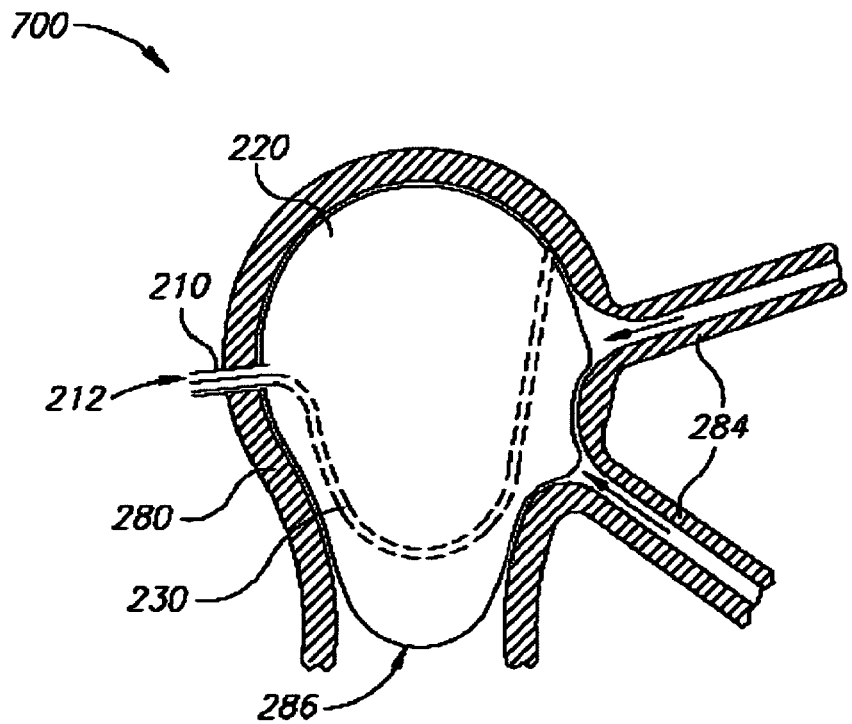
FIGS. 7A-B are cross sectional views of a balloon according to an exemplary embodiment of the invention within an atrium, in inflated and deflated states respectively.
Figure 7B:
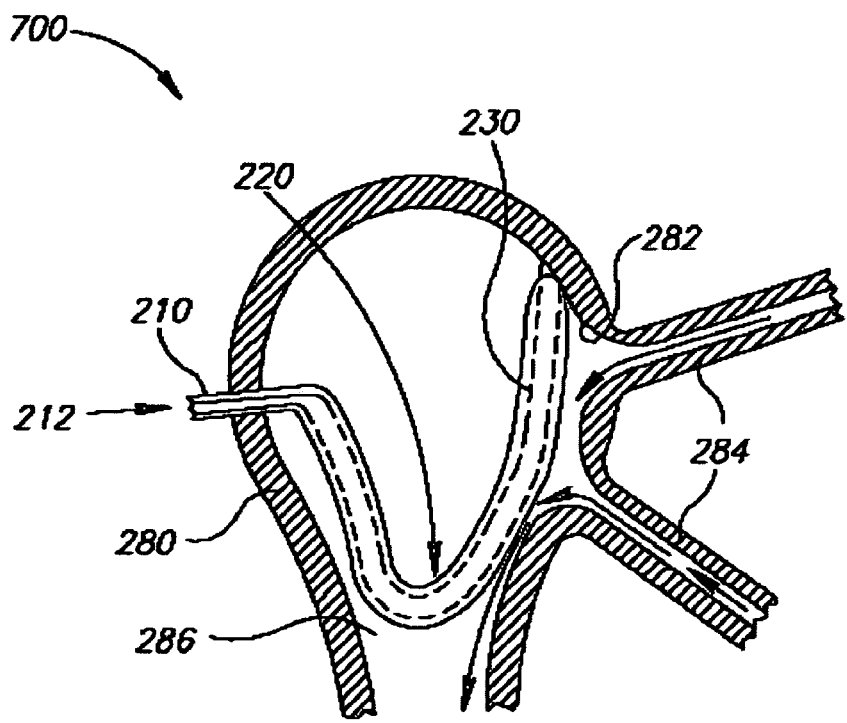

In an exemplary embodiment of the invention, blood flows from pulmonary veins 284 to mitral valve 286 during ablation (see, for example FIGS. 3C, 3D and 7B). Optionally, partial deflation 134 of balloon 220 contributes to an ability of blood to flow from pulmonary veins 284 to mitral valve 286 during ablation while ablation tool 230 continues to adhere or otherwise remain in contact 130 with the atrial wall. Optionally, channels in spacer 340 facilitate blood flow from pulmonary veins 284 to mitral valve 286 during ablation without partial deflation 134.

After the procedure is completed, balloon 220 is deflated and catheter 210 is withdrawn 136 together with balloon 220 and ablation tool 230.

In an exemplary embodiment of the invention, procedure 100 produces an ablation line which surrounds all four pulmonary veins 284 and, optionally, mitral valve 286.

In an exemplary embodiment of the invention, the ablation line is a hemiatrial ablation line which bisects the atria in a transverse plane through mitral valve 286 as depicted in FIG. 3D. Optionally, the ablation lines leave 50, 60, 70 or 80% or intermediate or greater percentages of atrial tissue in electrical contact with signals emanating from a SA node after formation of the ablation line, i.e., the signals reach the tissue.

In any of the above embodiments, ablation tool 230 can be mounted on, embedded in, disposed within, or disengaged from balloon 220. FIGS. 2E-H are fragmentary schematically illustrations showing several relations between ablation tool 230 and balloon 220. In FIG. 2E, ablation tool 230 is mounted on balloon 220, in FIG. 2F ablation tool 230 is embedded with the wall 221 of balloon 220, in FIG. 2G ablation tool 230 is disposed within the inner cavity 223 of balloon 220, and in FIG. 2H ablation tool 230 is disengaged from balloon 220 (e.g., ablation tool 230 and balloon 220 are devoid of contact thereamongst).

Exemplary Flow Through Ablation Apparatus

Figure 2C:
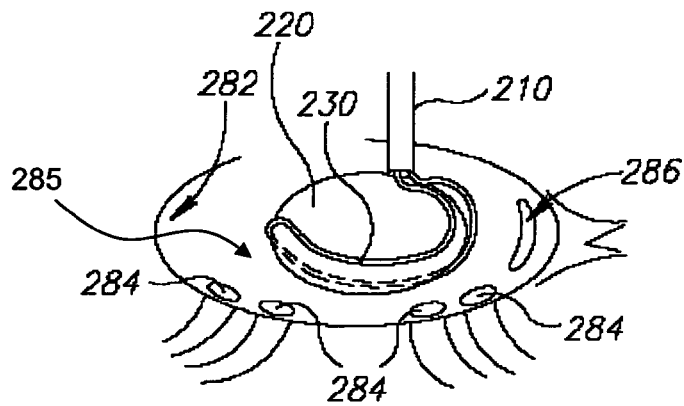
FIGS. 2C-D are cross sections of an atrium with an exemplary balloon and ablation catheter according to FIGS. 2A and 2B positioned in proximity to pulmonary veins in un-inflated and inflated states respectively.
Figure 2D:
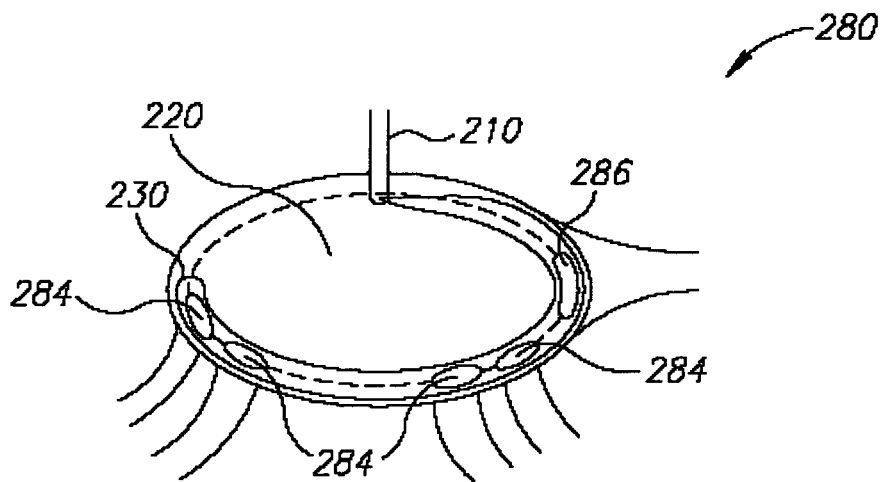

Referring now to FIGS. 3A, 3B and 3C, an exemplary flow-through apparatus 202 is described. Flow-through apparatus 202 is a variant of apparatus 200, depicted in FIGS. 2A, 2B, 2C and 2D. Similarly to apparatus 200, apparatus 202 includes balloon 220 and ablation tool 230 where ablation tool 230 can be mounted on, embedded in, disposed within, or disengaged from balloon 220 as further detailed hereinabove. Apparatus 202 further comprises a spacer 340 disposed between balloon 220 and ablation tool 230, such that spacer 340 touches inner wall 282 of atrium 280 around openings of pulmonary veins 284 without blocking the openings. Optionally, this configuration provides an open path for a flow of blood from pulmonary veins 284 to mitral valve 286 when balloon 220 is inflated by assuring that a portion of balloon 220 within a loop of ablation tool 230 does not contact pulmonary veins 284.

FIG. 3A is a side view of flow through ablation apparatus 202 protruding from a distal end 214 of catheter 210. Balloon 220 is inflated so that ablation tool 230 is expanded to its operative size (e.g. to form a loop). In this view it is clear that a thickness of spacer 340 is optionally much greater than that of ablation tool 230. Optionally, spacer 340 is an inflatable balloon or is constructed of compressible material with an elastic memory.

In an exemplary embodiment of the invention, spacer 340 functions as an insulation layer which protects main balloon 220 and/or circulating blood from undesired temperature changes which might result from contact with ablation tool 230. In some embodiments of the present invention, ablation tool 230 ablates tissue being in contact therewith by generating sufficient heat flow from the tissue to ablation tool 230, or by generating sufficient heat flow from ablation tool 230 to the tissue. For example, in some exemplary embodiments of the invention, ablation tool 230 is a cryo-ablation tool 230. In other exemplary embodiments of the invention, ablation tool 230 is a heat ablation tool 230. Several configurations which allow heat exchange between ablation tool 230 and the contacting tissue are described hereinunder with reference to FIGS. 9A-F.

When a cryo-ablation tool is employed, spacer 340 preferably prevents freezing of main balloon 220 and/or circulating blood. Freezing of main balloon 220 could compromise its structural integrity and/or make it difficult to remove balloon 220 after an ablation procedure.

When a heat ablation tool is employed, spacer 340 preferably prevents melting or burning of main balloon 220 and/or blood denaturation. Melting or burning of main balloon 220 could compromise its structural integrity. Denaturing of blood can cause unwanted, optionally dangerous, blood clots. Heat ablation tool 230 may employ a variety of energy sources to generate heat including, but not limited to, electric current, ultrasound and radio frequency energy.

FIG. 3B depicts a front view of flow through apparatus 202 with pulmonary veins 284 and mitral valve 286 in the foreground. In this view, the atrial wall is not shown for clarity. This view clearly shows that the loop of ablation tool 230 surrounds all four pulmonary veins 284 and, optionally, also mitral valve 286.

FIG. 3C shows a flow through apparatus 202 deployed in atrium 280 in a transverse cross section through line A-A of FIG. 3B. This view demonstrates how spacer 340 contacts inner wall 282 of atrium 280. Because spacer 340 surrounds all four pulmonary veins 284 (see FIG. 3B) and mitral valve 286 a flow of blood (indicated by arrows) from pulmonary veins 284 to mitral valve 286 continues even when main balloon 220 is fully inflated. In the transverse cross section, spacer 340 appears to "cover" pulmonary veins 284. However, spacer 340 is "in front of" veins 284 so that blood flow continues "behind" spacer 340, as can be understood by comparing FIGS. 3C and 3B.

FIG. 3D shows an additional exemplary embodiment 204 of a flow through balloon inflated in atrium 280. In the depicted embodiment rings 222 hold the loop of tool 230 to main balloon 220 as the balloon expands. Because ablation tool 230 describes a hemi-atrial circle, a flow of blood (indicated by arrows) from pulmonary veins 284 to mitral valve 286 continues even when main balloon 220 is fully inflated. In the depicted embodiment, balloon 220 is characterized by a disc or wheel configuration as opposed to the spheroid configuration of the previous figures.

Exemplary Steerable Balloon

FIGS. 4A-H are schematic illustrations of a balloon which can be employed by the method and apparatus of various exemplary embodiments of the present invention.

Figure 4A:
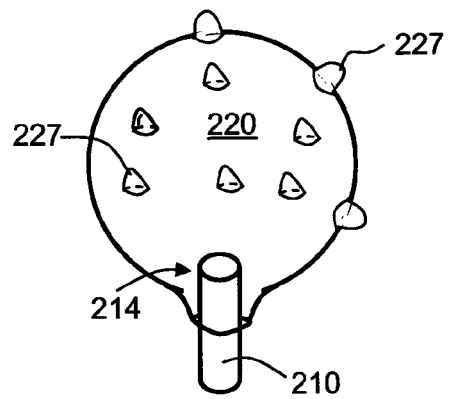
FIGS. 4A-K are schematic illustrations of a balloon according to various exemplary embodiments of the present invention.
Figure 4B:
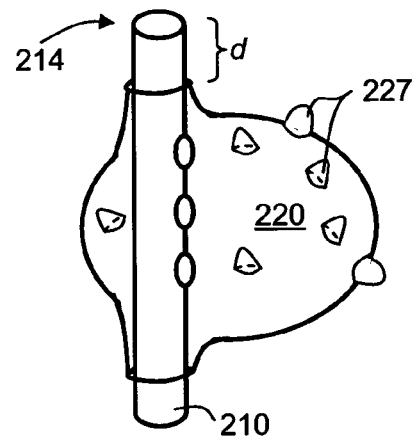
Figure 4C:
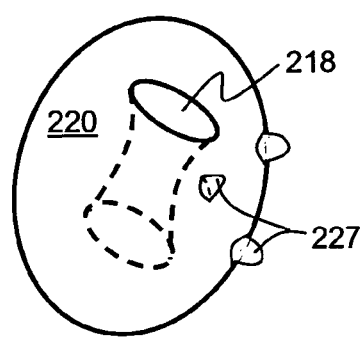
Figure 4D:
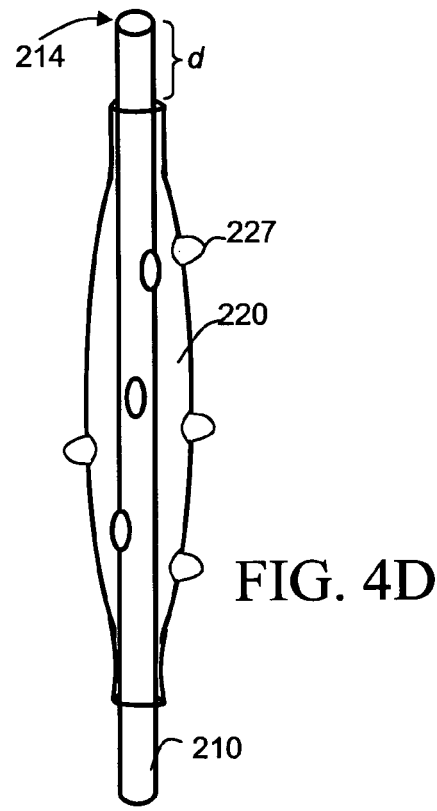

FIG. 4A illustrates an embodiments in which balloon 220 is generally spherically symmetric. FIG. 4B illustrates an embodiments in which balloon 220 is asymmetric with respect to catheter 210, where on one side of catheter 210 the balloon is inflated to a larger extent than on the other side thereof. FIG. 4C illustrates an embodiment in which balloon 220 includes a lumen 218. In this embodiment, balloon 220 is preferably deployed in the atrium such that when balloon 220 is in its inflated state one end of lumen 218 approximately faces the pulmonary veins and the other end of lumen 218 approximately faces the mitral valve. Thus, lumen 218 establishes fluid communication between the pulmonary veins and the mitral valve. FIG. 4D illustrates an embodiment in which balloon 220 is elongated. Balloon 220 can be mounted at distal end 214 of the catheter (as shown, for example, in FIG. 4A), or at a distance d from distal end 214 (as shown, for example, in FIGS. 4B and 4D).

In each of the embodiments of the present invention balloon 220 can include structural elements which facilitate blood flow between the wall of the atrium and the balloon's surface portion which contacts the wall.

For example, in some embodiments of the present invention the structural elements comprise a plurality of protrusions 227 extending from the surface balloon 220. The protrusions may be disposed regularly or irregularly about the body portion of balloon 220. Protrusions 227 serve for facilitating attachment of balloon 220 to the inner wall of the atrium while allowing blood flow. In use, balloon 220 is inflated until protrusions 227 contact or pressed against the inner wall of the atrium, such that a gap is formed between the atrium wall and regions on surface of balloon which are devoid of protrusions. Blood can then flow in the gap. The shape of the protrusions can be generally cylindrical, generally pyramidal, generally conical, generally frustoconical, and the like.

Figure 4E:
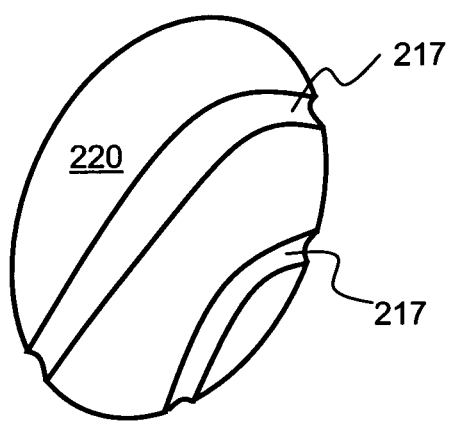
Figure 4F:
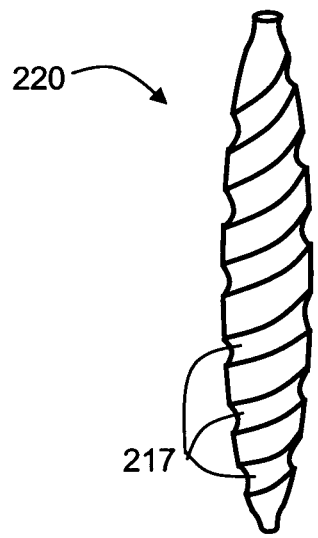

In some embodiments of the present invention the structural elements comprise slits formed on its surface so as to allow blood flow in the slits. This embodiment is illustrated in FIG. 4E, showing balloon 220 with slits 217 formed on its surface. Slits 217 serve for facilitating attachment of balloon 220 to the inner wall of the atrium while allowing blood flow. In use, balloon 220 is inflated until its surface contacts or pressed against the inner wall of the atrium. Blood can then flow in slits 217. The profile of the slits can be of any shape including generally rectangle, generally hemicylinderical, and the like. Slits 217 can be arranged on the surface of balloon 220 in any arrangement. For example, In some embodiments of the present invention slits 217 are arranged in a helical or screw-like arrangement, as schematically illustrated in FIG. 4F.

As stated, Balloon 220 can be made stretchable (e.g., elastic) or non-stretchable with a certain degree of characteristic strain. Catheter balloons with sufficiently low characteristic strains are oftentimes referred to in the literature as "non-compliant" balloons.

The term "non-compliant" when made in reference to a catheter balloon refers to a body which does not substantially stretch when inflated with fluid. A "non-compliant" balloon has a particular characteristic distended profile and it does not inflate beyond the characteristic distended profile by more than about 20%, more preferably 15%.

As used herein the term "about" refers to ±10%.

A "non-compliant" balloon remains at a preselected size and profile even when the internal pressure in the balloon is increased above that required to fully inflate the balloon. Suitable non-compliant structural polymeric materials for "non-compliant" balloon include, without limitation, modified polyesters, polyethylene terephthalate (PET), modified polybutylenes, polyvinyl chlorides, polyamides (e.g., Nylon), etc. Also contemplated are combinations of the structural polymeric materials listed above.

Catheter balloons with low characteristic strain, e.g., are "non-compliant" balloon are particularly useful in embodiments in which the surface of the balloon comprises structural elements which facilitate blood flow between the balloon and the wall of the atrium. For example, when balloon 220 includes slits 217 is can be a "non-compliant" balloon.

Figure 4G:
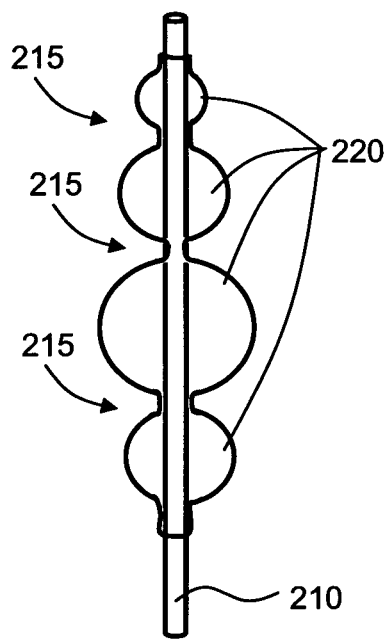

Balloon 220 can also comprises an arrangement of balloons as schematically illustrated in FIG. 4G. In this embodiment, blood can flow in spaces 215 formed between adjacent balloons.

Figure 4H:
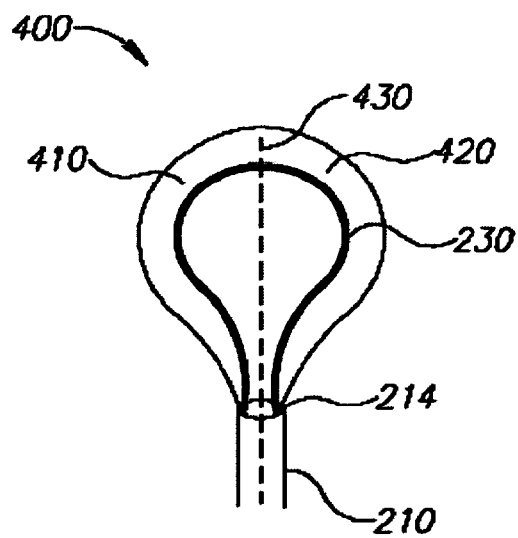
Figure 4I:
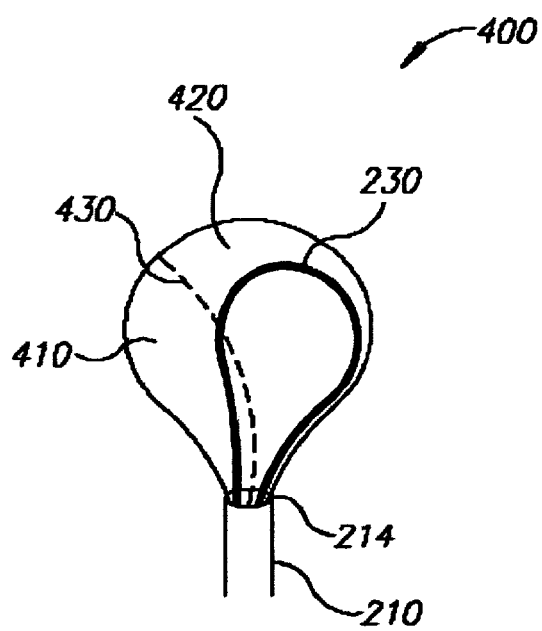
Figure 4J:
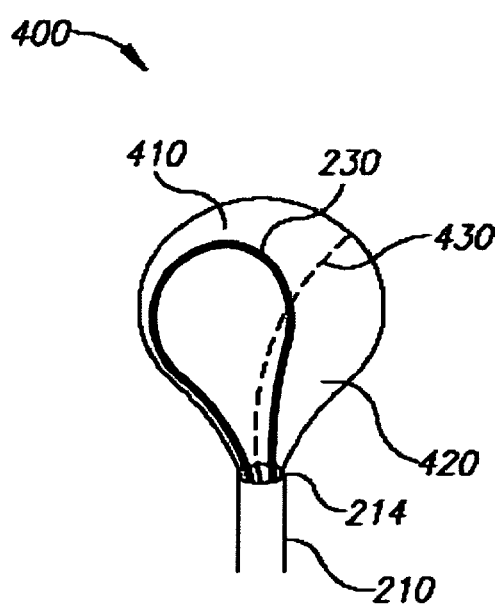

FIGS. 4H, 4i and 4J illustrate an exemplary balloon 400 comprising at least two independently inflatable chambers 410 and 420 separated by a common wall 430.

In all three figures, ablation tool 230 is mounted on chambers 410 and 420 of balloon 400 so that it is influenced by inflation of balloon 400. The same effect can be achieved when ablation tool 230 is embedded in the wall of balloon 400. Thus, although the ablation tool is shown as mounted on balloon 400 in FIGS. 4H-J, this need not necessarily be the case, since ablation tool 230 can be embedded in the wall or internal cavity of balloon 400 as further detailed hereinabove. Balloon 400 is inflated by an inflation controller 600 (FIG. 6) adapted to independently inflate each of chambers 410 and 420 of balloon 400. Controller 600 is described in greater detail hereinbelow in the context of FIG. 6.

FIG. 4H shows that when chambers 410 and 420 are equally inflated, ablation tool 230 forms a loop which is bilaterally symmetric with respect to common wall 430.

FIGS. 4i and 4J illustrate how a relative position of ablation tool 230 with respect to an intra-atrial target is adjustable by regulating a degree of inflation of each of chambers 410 and 420 of the balloon.

In FIG. 4i a degree of inflation of chamber 420 is greater than a degree of inflation 410. As a result, the ablation tool 230 loop is shifted to the right.

In FIG. 4J a degree of inflation of chamber 410 is greater than a degree of inflation 420. As a result, the ablation tool 230 loop is shifted to the left.

Figure 4K:
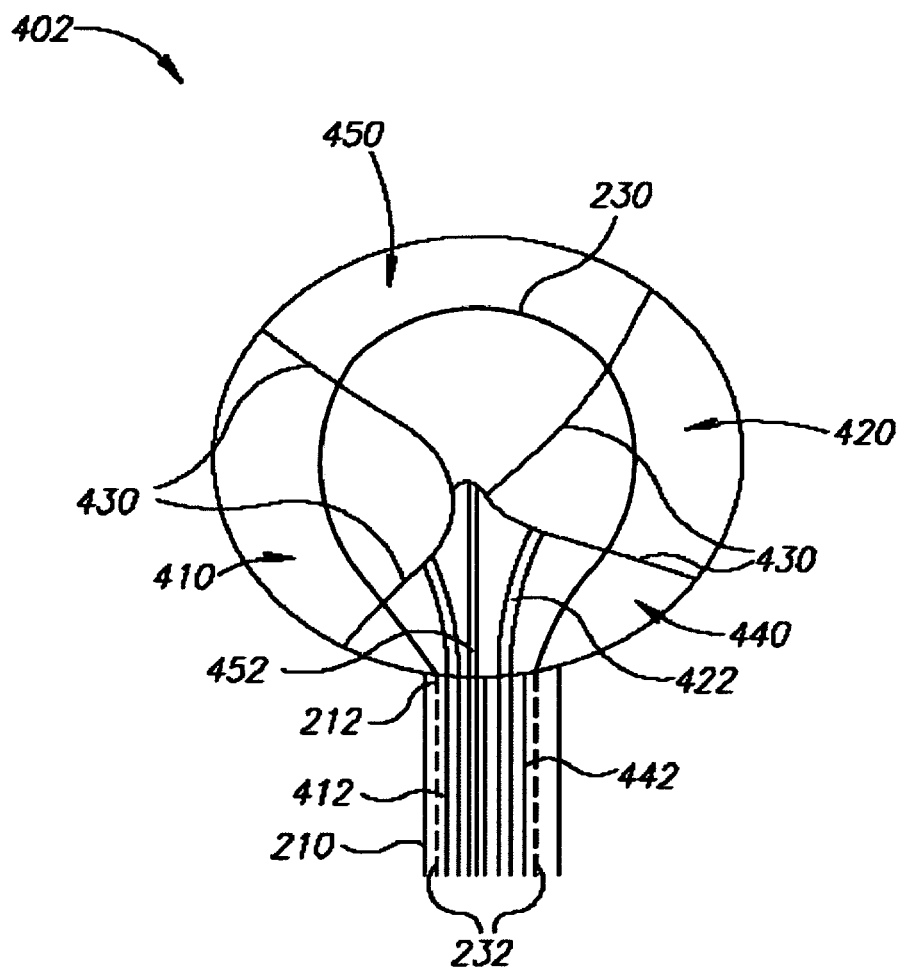

FIG. 4K illustrates an exemplary multi chamber balloon 402 comprising four independently inflatable chambers 410, 420, 440 and 450. Each of the four chambers is separated from its neighbors by a common wall 430.

In the pictured embodiment, each chamber 410, 420, 440 and 450 is in fluid communication with its own inflation lumen 412, 422, 442 and 452 respectively. Optionally, the inflation lumens are routed through catheter 210.

There is a tradeoff between the increased control over a shape of a loop of ablation tool 230 offered by an increasing number of chambers and the increased complexity of inflation patterns which must be implemented to realize the increased control. In an exemplary embodiment of the invention, the two compartment balloon 400 offers a sufficient degree of control over a shape of a loop of ablation tool 230 with an inflation program that is sufficiently simple to implement.

Exemplary Elastic Balloon with Flexible Ablation Element

FIGS. 2A, 2B, 2C and 2D illustrate an exemplary intra-atrial ablation therapy apparatus 200. In the depicted embodiment, apparatus 200 includes an elastic balloon 220 adapted for intra-atrial inflation and an ablation tool 230 passing through a plurality of rings 222 attached, integrally formed with, or connected to a net stretched on a surface of balloon 220. In an exemplary embodiment of the invention ablation tool 230 passes through rings 222 so that inflation of balloon 220 causes tool 230 to expand.

In an exemplary embodiment of the invention, inflation of balloon 220 is via an inflation pump 600 (FIG. 6) in fluid communication with balloon 220 and operable to provide a flow of an inflation fluid to the balloon. Pump 600 is described in greater detail hereinbelow.

FIG. 2A is a side view of apparatus 200 showing a catheter 210 with balloon 220 protruding from distal end 214 thereof. In the depicted embodiment, rings 222 attached to balloon 220 engage ablation tool 230. But this need not necessarily be the case as further detailed hereinunder. In the depicted embodiment a catheter lumen 212 contains an inflation lumen 224 for balloon 220 and additional material 232 for tool 230.

FIG. 2B is front view of apparatus 200 of FIG. 2A.

FIG. 2C illustrates a deflated apparatus 200 deployed in an atria 280 and positioned so that tool 230 will surround pulmonary veins 284 and optionally also encompass at least a portion of mitral valve 286 when expanded to contact inner atrial wall 282.

Figure 2E:
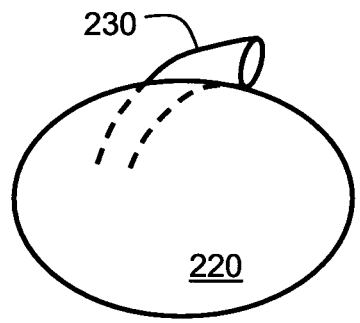
FIGS. 2E-H are fragmentary schematically illustrations showing several relations between an exemplary ablation tool and an exemplary balloon, according to various exemplary embodiments of the present invention.
Figure 2F:
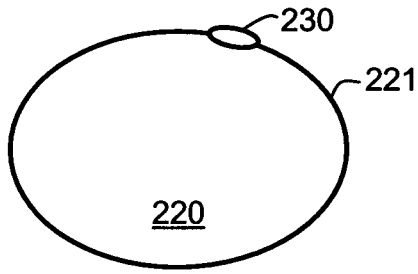
Figure 2G:
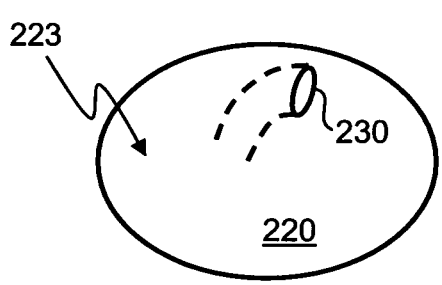
Figure 2H:
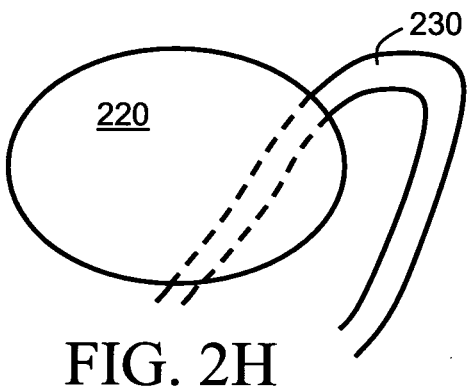

FIG. 2D illustrates an inflated apparatus 200 deployed in atria 280 so that a loop of ablation tool 230 surrounds pulmonary veins 284 and optionally also encompass at least a portion of mitral valve 286.

In an exemplary embodiment of the invention, ablation tool 230 is operated when it contacts inner wall 282 of atria 280 so that it forms an ablation line surrounding pulmonary veins 284 and optionally mitral valve 286.

FIGS. 8A and 8B illustrate an exemplary intra-atrial ablation therapy apparatus 800.

In FIG. 8A, balloon 220 of apparatus 800 is deflated so that distances between rings 222 are small. As described above, each of rings 222 engages ablation tool 230. In the depicted embodiment, a additional material 232 of tool 230 is stored within catheter 210.

In FIG. 8B, balloon 220 of apparatus 800 is inflated so that distances between rings 222 are increased relative to FIG. 8A. Since each of rings 222 engages ablation tool 230, a loop formed by tool 230 is expanded and/or altered in shape. In an exemplary embodiment of the invention, at least some of additional material 232 of tool 230 pulled from within catheter 210 when balloon 220 expands.

In an exemplary embodiment of the invention, each of rings 220 defines an engagement point which is fixed with respect to balloon 220 and dynamic with respect to ablation tool 230.

Optionally, ablation tool comprises a cryo-ablation element. In an exemplary embodiment of the invention, ablation tool is constructed primarily of a metal.

Exemplary Collapsing Balloon

FIGS. 7A and 7B illustrate an exemplary apparatus 700 adapted to perform intra-atrial ablation. A catheter 210 of apparatus 700 is inserted into atria 280, optionally via a trans-septal route. A balloon 220 and ablation tool 230 are deployed from a distal end of catheter 210. Balloon 220 is inflated so that a loop of tool 230 contacts tissue surrounding a target. At this stage ablation tool 230 is activated to form an ablation line around the target (e.g. all four pulmonary veins 284 or all four pulmonary veins 284 plus at least a portion of mitral valve 286).

However, as seen in FIG. 7A, inflated balloon 220 blocks a flow of blood from pulmonary veins 284 to mitral valve 286.

Therefore, in an exemplary embodiment of the invention, balloon 220 is partially deflated after ablation tool 230 adheres to tissue surrounding the target on inner wall 282 of atria 280 as depicted in FIG. 7B. This partial deflation permits a flow of blood (depicted by arrows) from pulmonary veins 284 to mitral valve 286. In an exemplary embodiment of the invention, tool 230 adheres to inner wall 282 of atrium 280 with sufficient force that contraction of balloon 220 does not cause it to disengage.

In an exemplary embodiment of the invention, ablation tool 230 is a cryo-ablation tool. Optionally, tool 230 is activated by causing a flow of a cold fluid (e.g., cryogenic fluid) through the ablation tool. In an exemplary embodiment of the invention, chilling of the ablation tool causes the tissue to freeze and the ablation tool 230 to adhere to the frozen tissue of the inner wall 282 of atria 280.

In an exemplary embodiment of the invention, ablation tool 230 is a heat ablation tool. Optionally, tool 230 is activated by causing an electric current to flow is through the tool so that it heats. In an exemplary embodiment of the invention, heating of the ablation tool causes the tissue to be scorched and/or emit a sticky fluid which allows the ablation tool 230 to adhere to inner wall 282 of atria 280.

Alternatively, or additionally, tool 230 adheres by using small anchors or hooks that attach to the tissue and/or glue.

Exemplary Orientation Confirmation by Contrast Solution Injection

Figure 5:
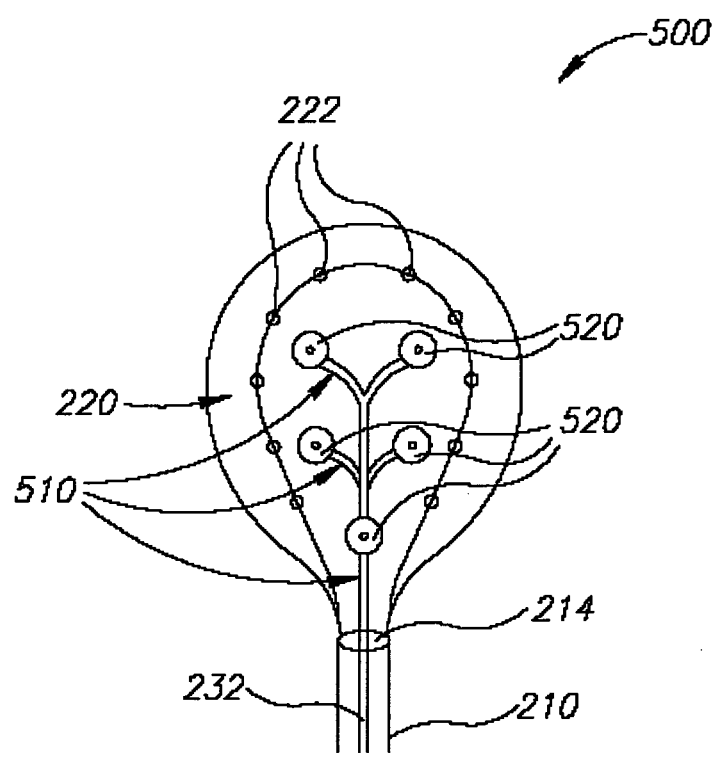
FIG. 5 is a front view of a balloon catheter adapted to eject dye according to an exemplary embodiment of the invention.

FIG. 5 illustrates an exemplary apparatus 500 for verifying a placement of an ablation tool. In the depicted embodiment, apparatus 500 comprises an expandable balloon 220 on which ablation tool 230 and at least one contrast solution channel 510 including at least one contrast injection port 520 (five are shown) are mounted.

In an exemplary embodiment of the invention, apparatus 500 also comprises a contrast injector 670 (FIG. 6) adapted to inject contrast solution from the at least one contrast injection port 520 and an imaging module 680 adapted to image the contrast solution.

In an exemplary embodiment of the invention, ablation tool 230 is configured as a loop and the at least one contrast injection port 520 is positioned within the loop.

In an exemplary embodiment of the invention, imaging module 680 comprises a fluoroscopy device.

In an exemplary embodiment of the invention, imaging module 680 is aimed to provide an image of pulmonary veins 284 and presence of contrast solution in the pulmonary veins indicates a correct placement of ablation tool 230. Optionally, the contrast agent is injected from injection ports 520 with sufficient force to overcome a flow of blood from vessels 284 to valve 286 so that some of the contrast enters vessel 284. Alternatively, or additionally, a flow of blood from vessel 284 to valve 286 can be cyclic so that contrast agent can enter vessel 284 in a part of the cycle when flow is diminished or absent.

Exemplary System with Controller

Figure 6:
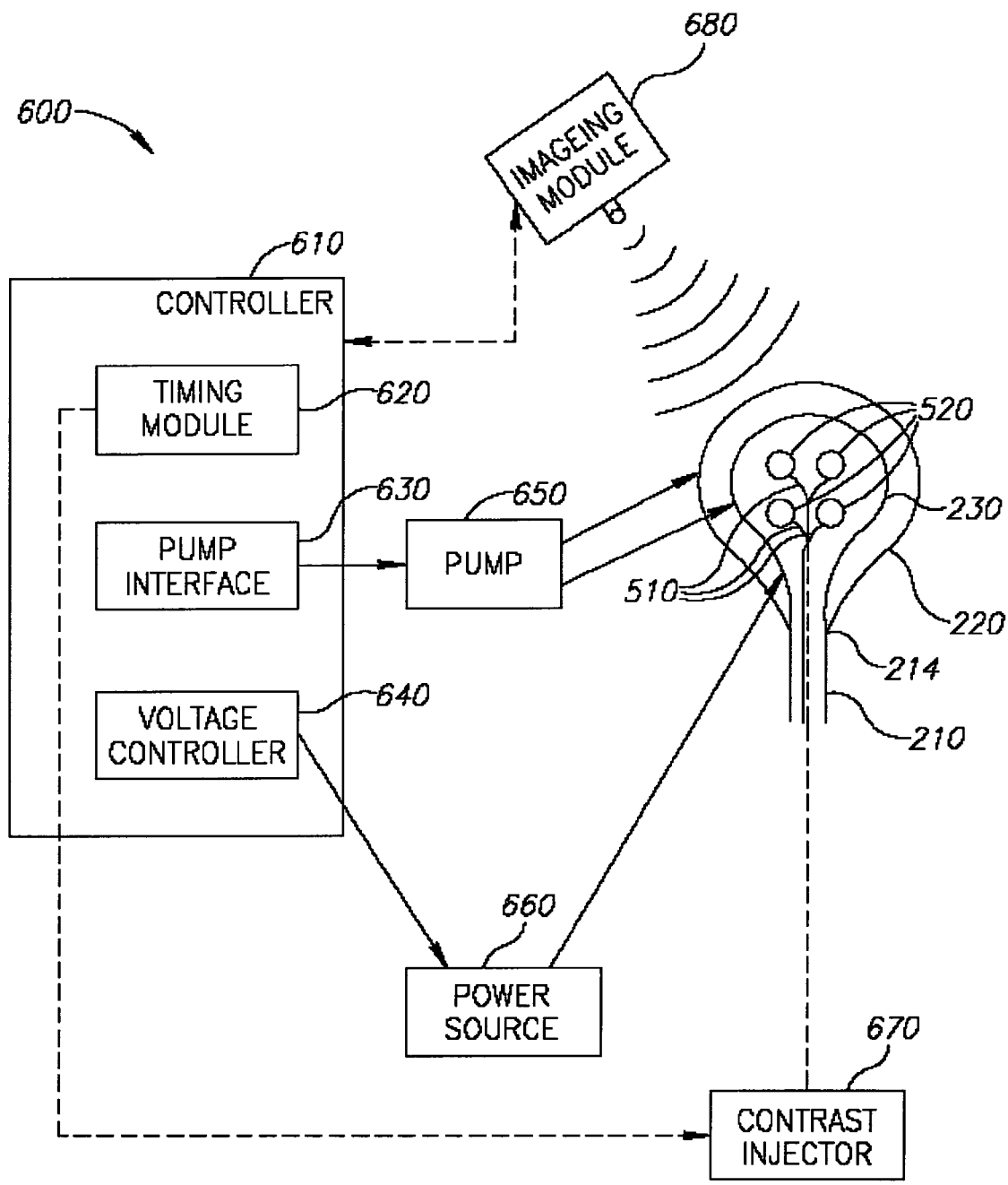
FIG. 6 is a schematic illustration of a system, including a controller, operably coupled to an intra-atrial ablation apparatus according to an exemplary embodiment of the invention.

FIG. 6 is a schematic representation of a system 600 including a controller 610 operably coupled to an intra-atrial ablation apparatus according to an exemplary embodiment.

In the depicted embodiment the intra atrial ablation apparatus comprises a balloon 220 and ablation tool 230 protruding from a distal end 214 of catheter 210 as described above. Optionally, contrast channel 510 and contrast injection ports 520 are provided as described above.

In an exemplary embodiment of the invention, controller 610 includes a pump interface 630. Optionally, pump interface 630 provides instructions to one or more pumps 650 (one is pictured). Pump interface 630 can control inflation of balloon 220 and/or a flow of cooling fluid in ablation tool 230. In those exemplary embodiments of the invention in which balloon 220 is divided into compartments, pump interface 630 controls inflation of each compartment separately. Optionally, Pump interface 630 also implements deflation of balloon 220, or compartments thereof.

In some exemplary embodiments of the invention, ablation tool is provided as an electro-ablation element. Optionally, controller 610 includes a voltage controller 640. Voltage control module 640 operates a power source 660 which sends an electric current through ablation tool 230 when the voltage controller is operated.

In those exemplary embodiments of the invention which include contrast channel 510 and contrast injection ports 520, system 600 includes a contrast injector 670. Contrast injector 670 is pictured as a separate unit, although it can optionally be integrated into a housing of controller 610 and/or be subject to control of controller 610. Optionally, injector 670 is a manually operated device, such as a syringe.

In an exemplary embodiment of the invention, controller 610 includes a timing module 620. In various exemplary embodiments of the invention, timing module 620 exercises temporal control over one or more of pump interface 630, voltage control module 640, and injector 670. In an exemplary embodiment of the invention, temporal control insures that ablation tool 230 is activated after balloon 220 is inflated and/or after a position of tool 230 has been deemed satisfactory. Alternatively, or additionally, timing module 620 governs how long ablation tool 230 remains active so that ablation occurs only to a desired degree.

System 600 includes an imaging module 680, optionally including a fluoroscopy unit.

In an exemplary embodiment of the invention, imaging module 680 provides an output to controller 610. Optionally, analytic circuitry in controller 610 analyzes the output to determine if ablation tool 230 is correctly oriented. Alternatively, or additionally, a human user of system 600 assesses a degree of orientation correctness based on a plurality of views.

In an exemplary embodiment of the invention, controller 610 inflates balloon 220 and/or activates ablation tool 230 based upon the analysis. In an exemplary embodiment of the invention, timing module 620 coordinates these activities according to a treatment plan.

Exemplary Ablation Tool

FIGS. 9A-E and 10A-D are fragmentary schematic illustrations showing several configurations for ablation tool 230. Typically, ablation tool is in the form of a curved tubular structure generally forming a loop. At least part of the loop (e.g., the part being in contact with the wall of the atrium) can be described geometrically as a toroidal shape 910. A toroidal shape is a solid generated by moving a closed curve 912 along generating line 914 (FIG. 9A). Curve 912 does not intersect or contain line 914. A toroidal shape is typically described mathematically using a toroidal coordinate system ($\xi, \eta, \psi$) shown in FIG. 9B.

For clarity of presentation the following conventions are used herein. A "longitudinal direction" refers to a direction tangential to a point on line 914. for example, when line 914 is a circle, the longitudinal direction can coincide with the first circumferential direction $\xi$ of the toroidal coordinate system. A "circumferential direction" refers to a direction tangential to a point on closed curve 912. For example, when curve 912 is a circle, the circumferential direction can coincide with the second circumferential direction $\psi$ of the toroidal coordinate system. For a given point on ablation tool 230, the circumferential direction is orthogonal to the longitudinal direction. A "radial direction" refers to a direction which is orthogonal to both the circumferential and the longitudinal directions for every point on tool 230.

A "radial cross-section" refers to a section through toroidal shape 910 in a plane containing closed curve 912 (see FIG. 9C). An "azimuthal angle" $\phi$ ($0 \leq \phi \leq 360°$) is defined in a radial cross-section as an angle between two radius-vectors pointing from the center of the radial cross-section to points on closed curve 912. A "longitudinal section" of tool 230 refers to a surface which is a portion of toroidal shape 910 between two radial cross-sections (see FIG. 9D). A longitudinal section is characterized by a length along the longitudinal direction. A "circumferential section" of tool 230 refers to a sectional surface of a longitudinal section which is on one side of a plane parallel to (but not necessarily containing) line 914 (see FIG. 9E). A circumferential section is characterized by a length L along the longitudinal direction and an azimuth angle $\phi$. Two or more circumferential sections are said to be "complementary" if they complete a full circumference of ablation tool 230 about generating line 914. Thus, the sum of azimuth angles of complementary circumferential sections is $2\pi$ or $360°$.

When tool 230 is a cryo-ablation tool, its tubular shape allows flow of cryogenic fluid through its inner lumen. When tool 230 is a heat-ablation tool, its tubular shape allows delivery of ablative radiation through its internal lumen.

Figure 10A:
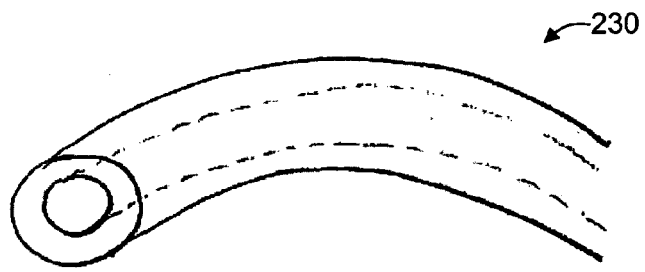
Figure 10B:
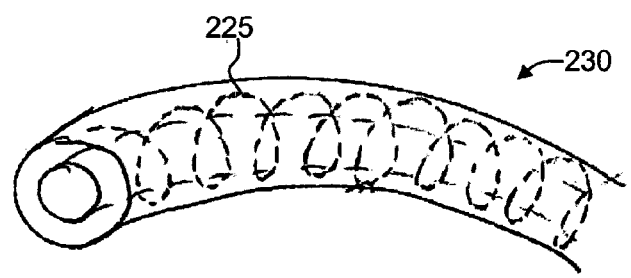
Figure 10C:
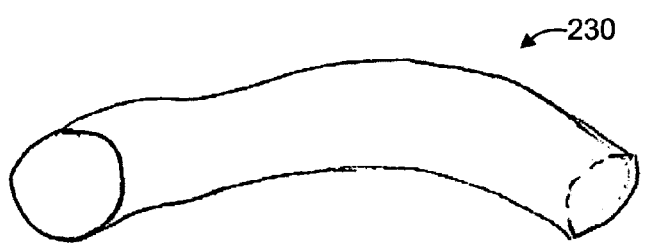
Figure 10D:
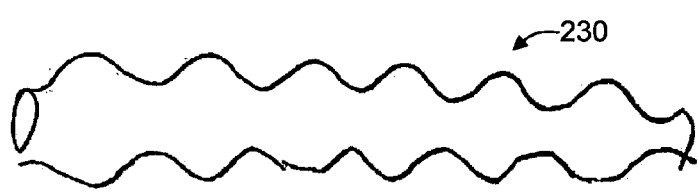

Tool 230 can be a tube made of a flexible material, such as, but not limited to, silicon or the like (FIG. 10A). Tool 230 can also be a reinforced tube having a reinforcing member 225 embedded in or mounted on the wall of tool 230 (FIG. 10B). Reinforcing member 225 can be, for example, a coiled pattern winding tool 230 in the circumferential direction and extending over its length or part thereof. In some embodiments, tool 230 is a made of a metallic foil (FIG. 10C). In some embodiments, tool 230 has a shape of a bellows (FIG. 10D) which can be made, for example, of a metal.

In various exemplary embodiments of the invention the length of ablation tool 230 is increasable to facilitate deployment thereof following the delivery to the atrium. This can be done in more than one way, as schematically illustrated in FIGS. 11A-H.

Figure 11A:
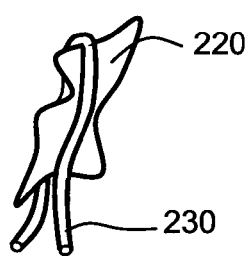
FIGS. 11A-$i$ are schematic illustrations of an expandable ablation tool, according to various exemplary embodiments of the present invention.
Figure 11B:
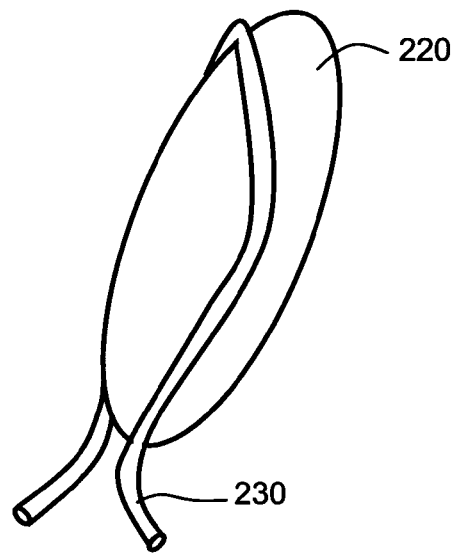
Figure 11C:
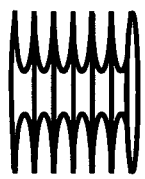
Figure 11D:
Figure 11E:
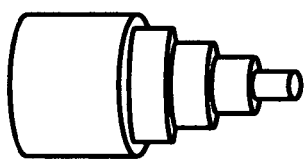
Figure 11F:
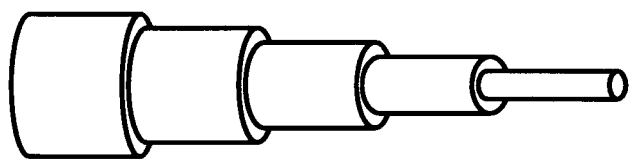

In some embodiments of the present invention ablation tool 230 is a longitudinally compliant structure such its length is increased or decreased in congruity with the inflation or deflation of balloon 220. This embodiment is generally illustrated in FIGS. 11A-B showing balloon 220 in its deflated (FIG. 11A) and inflated (FIG. 11B) state. As shown, when balloon 220 is in its deflated state ablation tool 230 is in its collapsed state and when balloon 220 is in its inflated state ablation tool 230 is in its stretched state.

A longitudinally compliant structure can be realized in more than one way.

In some embodiments of the present invention tool 230 is made of a material which is compliant (e.g., elastic) along the longitudinal direction.

In some embodiments of the present invention the compliance along the longitudinal direction ablation tool is realized by a bellows or telescopic structure which allows tool 230 to be stretched or collapse in congruity with the inflation of balloon 220. FIGS. 11C-F schematically illustrate exemplary embodiments in which ablation tool 230 is provided as a bellows (FIGS. 11C-D) and telescopic (FIGS. 11E-F) structure. Shown in FIGS. 11C-F are collapsed (FIGS. 11C and 11E) and stretched (FIGS. 11D and 11F) states of ablation tool 230. Balloon 220 is not shown in FIGS. 11C-F (see, e.g., FIGS. 11A-B).

Figure 11G:
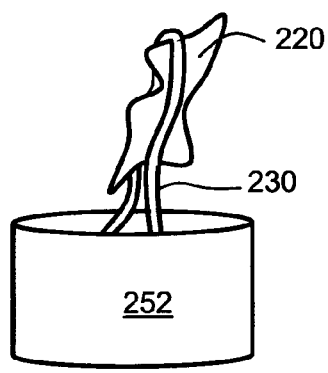
Figure 11H:
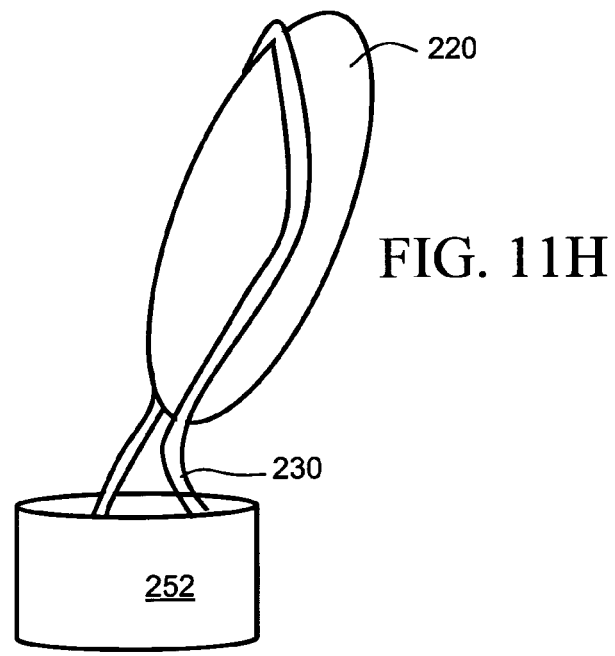
Figure 11I:
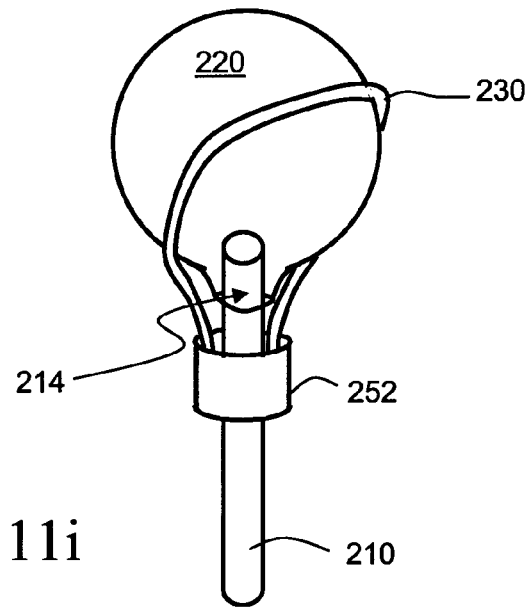

In some embodiments of the present invention the ablation tool is stored in a surplus compartment such that deployment of the ablation tool is facilitated by pulling the tubular structure forming the ablation tool out of the surplus compartment. This embodiment is illustrated in FIGS. 11G-*i* showing an exemplary surplus compartment 252 which stores surplus (not shown) of the tubular structure therein. When balloon 220 in its deflated state (FIG. 11G) the part of tool 230 which engages balloon 220 is short. Upon inflation of balloon 230 (FIG. 11H) surplus of tubular structure is being pulled out of compartment 252 and the length of ablation tool 230 is increased in congruity with the inflation of balloon 220. Compartment 252 can be mounted on or installed in the body of catheter 210, e.g., near distal end 214. A representative example for such configuration is illustrated in FIG. 11*i*.

FIGS. 12A-F are fragmentary schematic illustrations showing several configurations which allow heat exchange between ablation tool 230 and the contacting tissue. It is to be understood that although the embodiments described below and illustrated in FIGS. 12A-F are directed to a cryo-ablation tool, this need not necessarily be the case, since ablation tool 230 can, as stated, be also a heat ablation tool.

Figure 12A:
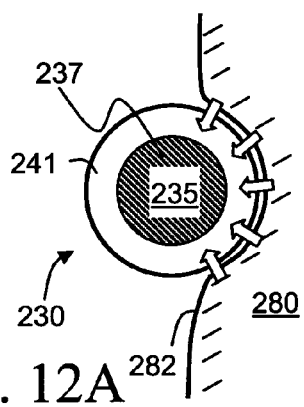
FIGS. 12A-F are schematic illustrations showing several configurations which allow heat exchange between an ablation tool and tissue, according to various exemplary embodiments of the present invention.

FIG. 12A schematically illustrates an embodiment in which a generally symmetric heat flow is employed. Shown in FIG. 12A is a cross-sectional view of a lumen 235 of cryoablation tool 230 contacting inner wall 282 of atrium 280. A cryogenic fluid 237 flows in lumen 235 in a direction perpendicular to the plane of FIG. 12A, and generate a heat flow from wall 280 to lumen 235. In this embodiment, at least part of the wall 241 of tool 230 is thermally conductive. Lumen 235 can be concentric or nonconcentric with the external surface of tool 230. FIG. 12A illustrates a concentric configuration in which the thickness of wall 241 is generally radially symmetric hence allow a heat flow which is generally radially symmetric. Nonconcentric embodiments of the present invention are described hereinunder (see FIGS. 12E and 12F). The heat flow is represented in FIG. 12A as block arrows. For clarity of presentation, the heat flow is not shown in FIGS. 12B-F.

In various exemplary embodiments of the invention ablation tool 230 conducts heat in an asymmetric manner. In these embodiments the amount of heat being conducted through one side of tool 230 is suppressed relative to the amount heat being conducted through the side thereof. From the standpoint of thermal conductivity, a longitudinal section of tool 230 is typically characterized in that the thermal conductivity of one circumferential section is higher than the thermal conductivity of the complementary circumferential section. For example, one circumferential section of tool 230 can be thermally conductive while the complementary circumferential section can be thermally isolating.

Figure 12B:
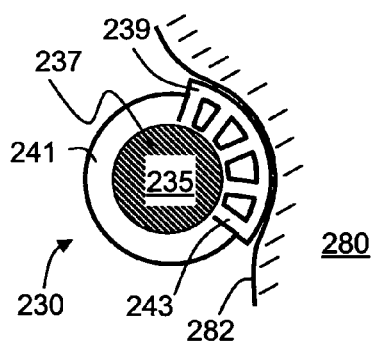
Figure 12C:
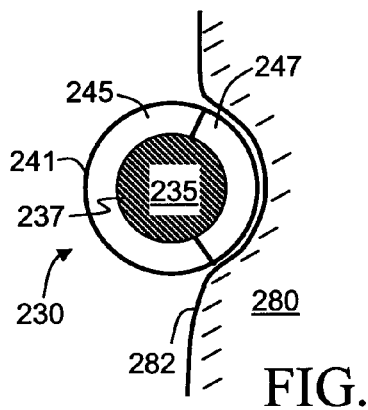

FIG. 12B schematically illustrates an embodiment in which heat is conveyed via a plurality of heat conducting channels within ablation tool 230. In this embodiment, ablation tool 230 comprises a heat conducting surface 239 which is brought into contact with inner wall 282 of atrium 280. The wall 241 of ablation tool 230 further comprises a plurality of openings 243 disposed along surface 239 to establish a continuous thermal path between surface 239 and cryogenic fluid 237. In this embodiment, wall 241 can be made thermally isolating such that heat flows through surface 239 and openings 243 is allowed and heat flow through other sections of wall 241 is prevented or at least reduced. Thus, the circumferential section which comprises surface 239 is thermally conductive while the complementary circumferential section is thermally isolating. FIG. 12C schematically illustrates an embodiment in which wall 241 of ablation tool 230 is made of a thermally isolating material 245 on one circumferential section and a thermally conducting material 247 on the complementary circumferential section. Thermally conducting material 247 is brought into contact with inner wall 282 of atrium 280, and thermally isolating material 245 can be in contact with the blood or balloon 220 (not shown). Cryogenic fluid 237 flows in lumen 235 in a direction perpendicular to the plane of FIG. 12C, and generate a heat flow through material 247 to lumen 235. Heat flow through material 245 is prevented or at least reduced.

Figure 12D:
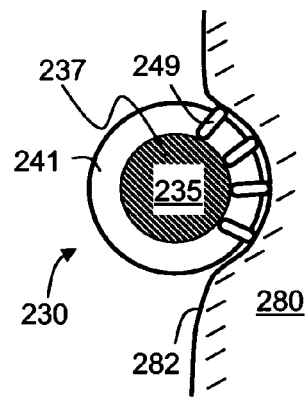

FIG. 12D schematically illustrates an embodiment in which heat is conveyed via a plurality of heat conducting elements 249 disposed in wall 241 of tool 230. The principles and operations of this embodiment are similar to the principles and operations of the embodiment shown in FIG. 12B described above, except that heat flows through elements 249. Thus, elements 249 are brought into contact with inner wall 282 of atrium 280, to establish a continuous thermal path between wall 282 and cryogenic fluid 237. Similar to the embodiment shown in FIG. 12B, wall 241 can be made thermally isolating such that heat flow through elements 249 is allowed and heat flow through other sections of wall 241 is prevented or at least reduced.

Figure 12E:
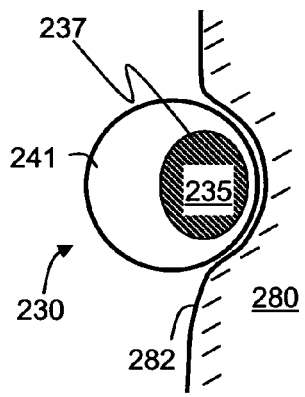

FIG. 12E schematically illustrates an embodiment in which a nonconcentric configuration is employed. Shown in FIG. 12E is a cross-sectional view of lumen 235 of cryoablation tool 230 contacting inner wall 282 of atrium 280. As shown the thickness of wall 241 of tool 230 is not radially symmetric such that lumen 235 is nonconcentric with the external surface of tool 231. Cryogenic fluid 237 flows in lumen 235 in a direction perpendicular to the plane of FIG. 12E, and generate a heat flow from wall 280 to lumen 235. The thinner side of wall 241 is brought into contact with inner wall 282 of atrium 280, and the thicker side of wall 241 can be in contact with the blood or balloon 220 (not shown). Since lumen 235 is nonconcentric with the external surface of tool 231 more heat flows through the thinner side of wall 241 than through the thicker side thereof.

Figure 12F:
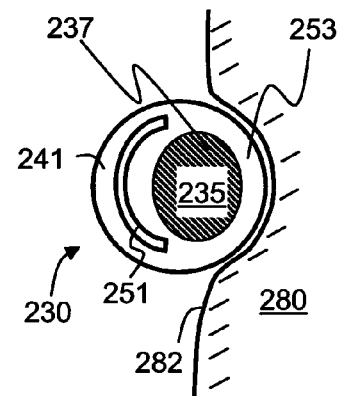

FIG. 12F schematically illustrates another embodiment in which tool 230 has a thermally conductive side and a thermally isolating side. In the exemplified embodiment illustrated in FIG. 12F, wall 241 is embedded with an internal thermally isolating layer 251. In this embodiment, the thickness of wall 241 can be either radially symmetric or radially asymmetric. In the non-limiting example illustrated in FIG. 12F the thickness of wall 241 is radially asymmetric such that lumen 235 is nonconcentric with the external surface of tool 231, but a symmetric thickness (such as the configuration illustrated in FIG. 12A) is also contemplated. Thermally isolating layer 251 is embedded in wall 241 such as to prevent or at least reduce heat flow from one side of tool 231. Thermally isolating layer 251 can be shaped, e.g., as a part of a cylinder (for example, a hemicylinder) and is preferably embedded in wall 241 so as to partially enclose lumen 235 while maintaining at least one continuous thermally conductive path 253 between lumen 235 and the external surface of wall 241. Thus, tool 230 has a thermally isolating side and a thermally conductive side. Tool 230 can be positioned such that the conductive path 235 contacts inner wall 282. Cryogenic fluid 237 flows in lumen 235 in a direction perpendicular to the plane of FIG. 12F, and generate a heat flow from wall 280 to lumen 235, through path 253. The thermally isolating side of wall 241 can be in contact with the blood or balloon 220 (not shown), such that layer 251 prevents or at least reduces heat flow from the balloon or the blood.

Various combinations of the above embodiments are also contemplated, and one of ordinary skill in the art would know how to construct tool 230 by combining features described above. For example, the embodiment illustrated in FIGS. 12E and/or 12F can be combined with any of the other embodiments by manufacturing tool 230 such that lumen 235 and wall 241 are non-concentric and/or by incorporating internal thermally isolating layer 251 in wall 241; the embodiment illustrated in FIG. 12D can be combined with the embodiment illustrated in FIG. 12B by replacing openings 243 with heat conducting elements 249; the embodiment illustrated in FIG. 12C can be combined with any of the other embodiments by manufacturing wall 241 such that it is made of thermally isolating material 245 on one circumferential section and thermally conducting material 247 on the complementary circumferential section; ant so on.

FIGS. 13A-E are schematic illustrations of connection types between tool 230 and balloon 220 according to various exemplary embodiments of the present invention. FIG. 13A illustrates an embodiment in which tool 230 is connected to balloon 220 by a plurality of rings 222; FIG. 13B illustrates an embodiment in which tool 230 is connected to balloon 220 via an adhesive layer 226; FIG. 13C illustrates an embodiment in which tool 230 is connected to balloon 220 by a string 228 which is fixed to balloon 220 via an arrangement of rings or loops 229.

In some embodiments of the present invention, the connection between ablation tool 230 and the balloon is sufficiently weak so as to allow disengagement of ablation tool 230 from balloon 220 once balloon is in its inflate state. This can be done in more than one way. For example, in embodiments in which adhesive layer 226 is employed, the adhesive can be selected sufficiently weak such that tension forces resulting from the inflation of the balloon are stronger than the adhesion strength of layer 226. Adhesive layer 226 can also be made from a biodegradable material. In embodiments in which rings 222 are employed, rings 222 can be loosely closed or be made elastic such that in the deflated state of balloon 220 rings 222 are closed (see FIG. 13D), but once balloon 220 is inflated rings 222 are opened and tool 230 is released therefrom (see FIG. 13E).

FIGS. 14A-D are schematic illustrations of embodiments in which the ablation tool and balloon 220 are initially disengaged, and the deployment of ablation tool at the ablation location is executed subsequently to the inflation of the balloon in the atrium. For clarity of presentation the atrium is not shown in FIGS. 14A-D.

FIGS. 14A-B are schematic illustrations of an embodiment in which balloon 220 includes a plurality of rings 222 connected thereto. A string or guidewire 272 engages rings 222 and is connected on one of its ends 274 to ablation tool 230 which is initially disengaged from balloon 220. Deployment of ablation tool 230 in the atrium is by pulling the other end 276 of guidewire 272. Rings 222 can be arranged to receive tool 230. In this embodiment guidewire 272 is pulled at least until it passes through one or more of the rings, for example, to assume the configuration shown in FIG. 13A. Alternatively, rings 222 can be arranged such that once tool 230 is not received thereby. In this embodiment, the pulling of guidewire 272 is stopped before tool 230 engages the first ring. The deployment of tool 230 in this embodiment is illustrated in FIG. 14B.

FIG. 14C is a schematic illustration of an embodiment which is similar to the embodiment illustrated in FIGS. 14A-B with exception that a net 278 is stretched over balloon 220. Rings 222 can then be connected to net 278 rather than directly to balloon 220.

FIG. 14D is a schematic illustration of an embodiment in which rings 222 are mounted on catheter 210 instead of balloon 220. Deployment of ablation tool 230 in the atrium is by pulling end 276 of guidewire 272 until tool 230 is appropriately deployed at the ablation location of the atrium.

Exemplary Catheter

Figure 15A:
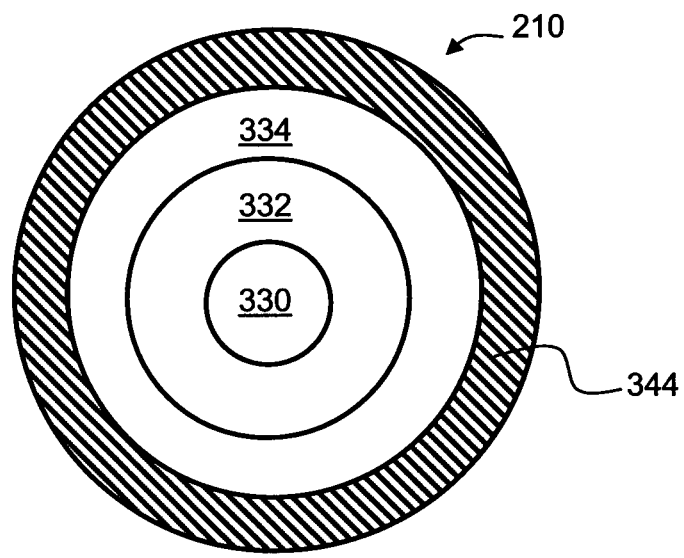
FIGS. 15A-B are schematic illustrations of a radial cross-section of a catheter according to various exemplary embodiments of the present invention.
Figure 15B:
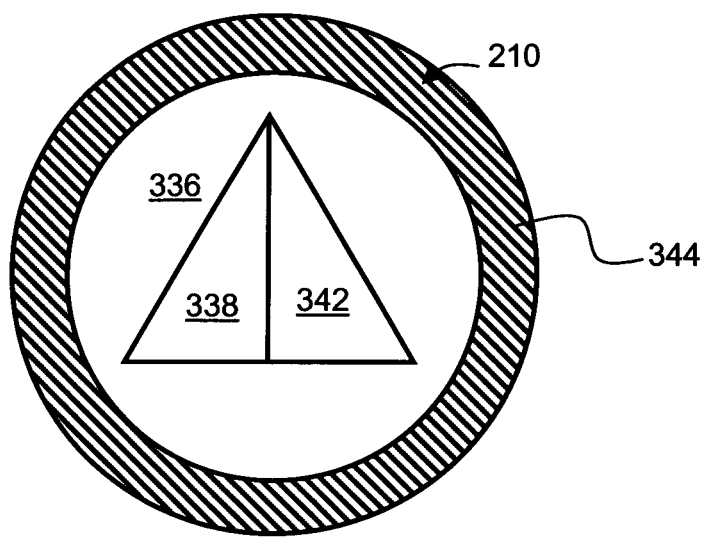

FIGS. 15A-B are schematic illustrations of a radial cross-section of catheter 210 according to various exemplary embodiments of the present invention.

FIG. 15A schematically illustrates an embodiment in which catheter 210 comprises three generally concentric flow lumens, 330, 332 and 334. Lumen 330 is the innermost lumen and it can be used for providing inflow of cryogenic fluid to ablation tool 230 (not shown). Lumen 332 is the intermediate lumen and it can be used for guiding outflow of cryogenic fluid from ablation tool 230. Lumen 334 is the outermost lumen and it can be used for delivering balloon inflating fluid to balloon 220 (not shown). In various exemplary embodiments of the invention lumens 330, 332 and 334 are in fluid communication with a pump, e.g., pump 630 (not shown).

FIG. 15B schematically illustrates an embodiment in which the radial cross section of catheter 210 is divided non-concentrically. In the representative illustration of FIG. 15B, catheter 210 comprises a main flow lumen 336 and two additional flow lumens 338 and 342 disposed in main lumen 336. Although FIG. 15B shows a triangular radial cross-section for lumens 338 and 342, this need not necessarily be the case, since the radial cross-section lumens 338 and 342 can have any other shape. Lumen 336 can be used for delivering balloon inflating fluid to the balloon, and lumens 338 and 342 can be used for providing inflow and outflow of cryogenic fluid to and from the ablation tool. In various exemplary embodiments of the invention lumens 336, 338 and 342 are in fluid communication with a pump.

In various exemplary embodiments of the invention catheter 210 has a peripheral thermal isolation layer 344 surrounding the flow region of catheter 210. Layer 344 can be made of a material having sufficiently low thermal conductivity, such as, but not limited to, a ceramic material. Layer 344 can also be embedded with objects or particles, such as glass beads, which reduce thermal conductivity. Layer 344 can also be made of foam material having closed or open cells. In some embodiment layer 344 is filled with gas. Alternatively layer 344 can be a vacuum layer.

It is expected that during the life of a patent maturing from this application many relevant catheter balloons and ablation tools will be developed and the scope of the terms "balloon" and "ablation tool" is intended to include all such new technologies a priori.

A variety of numerical indicators have been utilized to describe various components of the apparatus and/or relationships between the apparatus and a heart chamber (e.g. atrium). It should be understood that these numerical indicators could vary even further based upon a variety of engineering principles, materials, intended use and designs incorporated into the invention.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An intra-atrial ablation therapy apparatus comprising: a plurality of balloons adapted for intra-atrial inflation to fill at least part of an atrium, said plurality of balloons being adapted to permit a flow of blood from a pulmonary vein to a mitral valve when inflated in the atrium, wherein said plurality of balloons are adapted to be spaced within the atrium so as to permit blood flow between said plurality of balloons when inflated in the atrium; an inflation lumen being in fluid communication with said plurality of balloons and adapted for conducting an inflation fluid to said plurality of balloons, wherein said plurality of balloons is adapted to occupy at least 70% of an atrial volume when said plurality of balloons are adapted to be inflated in the atrium; an expandable ablation tool configured as a loop, and a catheter adapted to deliver the ablation tool and said plurality of balloons to the atrium, wherein inflation of at least one of said plurality of balloons causes said ablation tool to expand and move towards an ablation location in the atrium, further comprising an arrangement of adjacent rings installed on a surface of at least one of said plurality of balloons, said ablation tool passing through and engaging said adjacent rings such that inflation of said at least one of said plurality of balloons causes a distance between said adjacent rings to increase due to the inflation of said at least one of said plurality of balloons, thereby causing said ablation tool to expand due to said increase of said distance between said adjacent rings.

2. The apparatus of claim 1, wherein said ablation tool comprises a cryo-ablation element.

3. The apparatus of claim 1, wherein said ablation tool comprises an ablation element which ablates by heating.

\* \* \* \* \*